US006762030B2

(12) United States Patent
Lyman et al.

(10) Patent No.: US 6,762,030 B2
(45) Date of Patent: Jul. 13, 2004

(54) LIGAND FOR CD7 AND METHODS FOR USE THEREOF

(75) Inventors: Stewart D. Lyman, Seattle, WA (US); William C. Fanslow, III, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 09/997,165

(22) Filed: Nov. 27, 2001

(65) Prior Publication Data

US 2002/0141999 A1 Oct. 3, 2002

Related U.S. Application Data

(63) Continuation-in-part of application No. PCT/US00/14612, filed on May 26, 2000.
(60) Provisional application No. 60/136,450, filed on May 28, 1999.

(51) Int. Cl.[7] .......................... G01N 33/53; C12Q 3/00; C07K 16/00
(52) U.S. Cl. .......................... 435/7.1; 435/4; 530/388.7; 530/389.2
(58) Field of Search .................. 435/4, 7.1; 530/388.7, 530/389.2

(56) References Cited

FOREIGN PATENT DOCUMENTS

| WO | WO 98/22502 | 5/1998 |
| WO | WO 99/50297 | 10/1999 |

OTHER PUBLICATIONS

Aruffo, A. and Seed, B., "Molecular cloning of two CD7 (T–cell leukemia antigen)cDNAs by a COS cell expression system," *EMBO J.* 6(11):3313–3316, 1987.
Barcena, A. et al., "Tracing the expression of CD7 and other antigens during T– and myeloid–cell differentiation in the human fetal liver and thymus," *Leuk Lymphoma* 17:1–11, 1995.
Baum, W. et al., "Therapy with CD7 monoclonal antibody TH–69 is highly effective for xenografted human T–cell ALL," *Br. J. Haemotol.* 95:327–338, 1996.
Bonilla, F. et al., "Targeted gene disruption of murine CD7," *International Immunol.* 9(12):1875–1883, Jun. 1997.
Carrera, A. et al., "Triggering of co–mitogenic signals in T cell proliferation by anti–LFA–1 (CD18, CD11a), LFA–3, and CD7 monoclonal antibodies," *J. of Immunol.* 141(6):1919–1924, Sep. 1988.
Eiras, P. et al., "Flow cytometry description of a novel CD3–/CD7+ intraepithelial lymphocyte subset in human duodenal biopsies: Potential diagnostic value in coeliac disease," *Cytometry* 34:95–102, 1998.

Flavell, DJ et al, "Comparison of the potency and therapeitic efficacy of the anti–CD7 immunotoxin HB2–saporin constructed with one or two saporin moieties per immunotoxin molecule," *Br. J. Cancer* 75(7):1035–1043, 1997.
Frankel, A. et al., "Therapy of patients with T–cell lymphomas and leukemias using an anti–CD7 monoclonal antibody–ricin a chain immunotoxin," *Leuk & Lymphoma* 26:287–298, 1997.
Haynes, B. et al., "Ontogeny of T–cell precursors: a model for the initial stages of human T–cell development," *Immunol. Today* 10(3):87–91, 1989.
Haynes, B. et al., "Human intrathymic T cell differentiation," *Semin Immunol.* 2:67–77, 1990.
Hou, Z. et al., "Cross–linking CD7 on myeloblasts results in granulocyte–macrophage colony–stimulating factor production," *Blood* 88(1):124–129, 1996.
*Lazarovits, A. et al, "Human mouse chimeric CD7 monoclonal antibody (SDZCHH380) for the prophylaxis of kidney transplant rejection," *J. of Immunol.* 150(11):5163–5174, Jun. 1993.
Lazarovits, A. and Karsh, J., "A monoclonal antibody, 7G5 (CD7), induces modulation of Tp40 and inhibits proliferation in the allogeneic and autologous mixed lymphocyte reactions," *Transplant Proc.* 20(6):1253–1257, 1988.
Lee, D. et al., "Immunologic characterization of CD7–deficient mice," *J. of Immunol.* 160:5749–5756, 1998.
Leta, E. et al., "Interaction between the extracellular domain of CD7 and concanavalin A: A clue to the identity of the ligand for CD7," *Cellular Immunol.* 173(0247):15–21, 1996.
Leta, E. et al., "Production and characterization of the extracellular domain of human CD7 antigen: Further evidence that CD7 has a role in T cell signaling," *Cellular Immunol.* 165:101–109, 1995.
*Lyman, S. et al., "Identification of CD7 as a cognate of the human K12 (SECTM1) protein," *J. of Biol. Chem.* 275(5):3431–3437, Feb. 2000.
Osada, S. et al., "Assignment of a gene coding for a human T–cell antigen with a molecular weight of 40,000 daltons to chromosome 17," *Cytogenet Cell Genet* 47:8–10, 1988.
*Pauza, M. et al., "Construction and characterization of human CD7–specific single–chain Fv immunotoxins," *J. of Immunol.* 158:3259–3269, 1997.

(List continued on next page.)

*Primary Examiner*—James Housel
*Assistant Examiner*—Stacy B. Chen
(74) *Attorney, Agent, or Firm*—James E. Klaniecki

(57) ABSTRACT

The invention relates to CD7 and the discovery of its cognate ligand, the K12 protein, and the identification and cloning of polynucletides that encode the murine homolog of the human K12. Also disclosed are methods of screening candidate molecules to determine potential antagonists and agonists of the interaction between CD7 and K12. The use of the antagonists and agonists, including soluble K12 proteins, as therapeutics to treat diseases modulated by CD7 are also disclosed.

14 Claims, 2 Drawing Sheets

OTHER PUBLICATIONS

Rabinowich, H. et al., "Expression and function of CD7 molecule on human natural killer cells," *J. of Immunol.* 152:517–526, 1994.

*Rabinowich, H. et al., "Signaling via CD7 molecules on human NK cells: Induction of tyrosine phosphorylation and $\beta_1$ integrin–mediated adhesion to fibronectin," *J. of Immunol.* 153:3504–3513, 1994.

* Sato, A. et al., "Identification of CD7 glycoprotein as an accessory molecule in HIV–1–mediated syncytium formation and cellfree infection," *J. of Immunol.* 152:5142–5152, 1994.

Schanberg, L. et al., "Characterization of human CD7 transgenic mice," *J. of Immunol.* 155:2407–2418, 1995.

Sempowski, G. et al., "Resistance of CD7–deficient mice to lipopolysaccharide–induced shock syndromes," *J. Exp. Med.* 189(6): 1011–1016, Mar. 1999.

Shimizu, Y. et al., "Crosslinking of the T cell–specific accessory molecules CD7 and CD28 modulates T cell adhesion," *J. Exp. Med.* 175–1 :577–582, 1992.

*Slentz–Kesler, K. et al., Identification and characterization of K12 (SECTM1), a novel human gene that encodes a golgi–associated protein with transmembrane and secreted isoforms, *Genomics 47*:327–340, 1998.

Spencer, J. et al., "Chanes in intraepithelial lymphocyte subpopulations in coeliac disease and enteropathy associated T cell lymphoma (maligant histiocytosis of the intestine)," *Gut 30*:339–346, 1989.

Wiley, S. et al., "Reverse signaling via CD30 ligand," *J. of Immunol. 157*:3635–3639, 1996.

Yoshikawa, K. et al., "Molecular cloning of the gene coding for the human T cell differentiation antigen CD7," *Imunogenetics 33*:352–360, 1991.

Yoshikawa, K. et al., " Isolation and characterization of mouse CD7 cDNA," *Immunogenetics 37*:114–119, 1993.

Yoshikawa, K. et al., "Molecular cloning of the gene coding for themouse T–cell antigen CD7," *Immunogenetics 41*: 159–161, 1995.

```
Human    1  MQTCPLAFPGHVSQALGTLLFLAASLSAQNEGWDSPICTEGVVSVSWGEN  50
            |   . |  . | || |||||.| |: || | |||||  |||. |
Mouse    1  MLAYSVTSSGLFPRMLWALLLLAASLNAHNDVWDEPCQTEHEVSVNRGSR  50

Human   51  TVMSCNISNAFSHVNIKLRAHGQESAIFNEVAPGYFSRDGWQLQVQGGVA  100
            ||.|||||   | |.|   .| |||   ||:|:| ||| :|| |
Mouse   51  VVMACNISNNLRDVTIELVTSEKTSIIFNHTPPGNYSKDSWQLHIQGVQA  100

Human  101  QLVIKGARDSHAGLYMWHLVGHQRNNRQVTLEVSGAEPQSAPDTGFWPVP  150
            ||||  |.| |.| | | | |    :    | |.|:| |    ||
Mouse  101  QLVITDAQDKHSGNYSWKLHGFQAEFKNFNLTVNAADRQKTEDLPVTKVP  150

Human  151  .AVVTAVFILLVALVMFAWYRCRCS.QQRREKKFFLLEPQMKVAA.LRAG  197
             |||   .: ::   |              | | . ||....
Mouse  151  DKPPTAVRTEVIIIAIATTIIITGIGVFVWYKQFPVAPQIQMSVPCLIH  200

Human  198  AQQGLSRASAELWTPDSEPTPRPLALVFKPSPLGALELLSPQPLFPYAAD  247
               |:   .
Mouse  201  GSPGIPYLTLPP                                  :    212

Human  248  P
```

Fig. 1

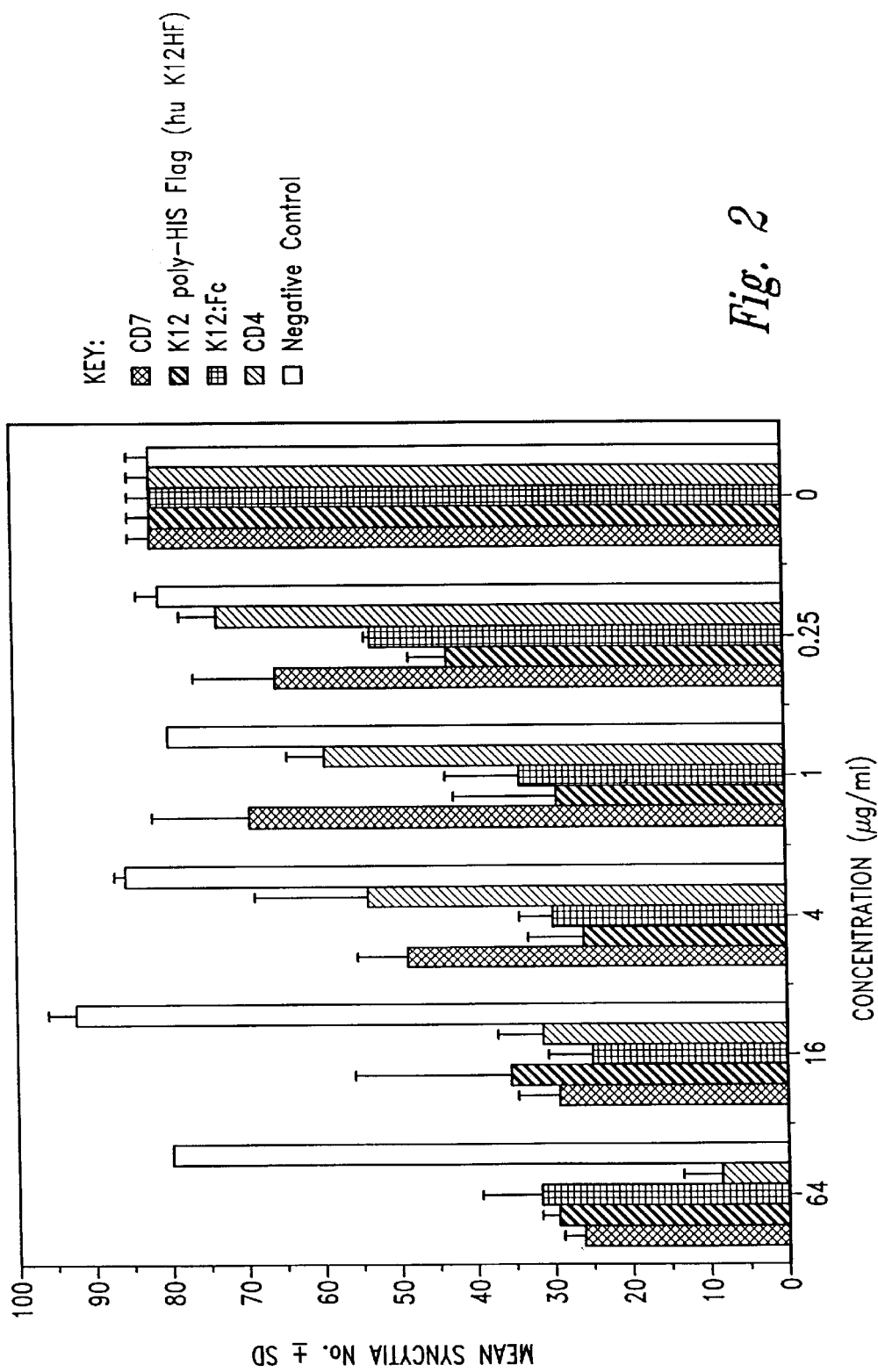

SEQUENCE LISTING

<160> NUMBER OF SEQ ID NOS: 8

<210> SEQ ID NO 1
<211> LENGTH: 1656
<212> TYPE: DNA
<213> ORGANISM: Homo sapiens

<400> SEQUENCE: 1

| | | | | | |
|---|---|---|---|---|---|
| tagacccaga | gaggctcagc | tgcactcgcc | cggctgggag | agctgggtgt | ggggaacatg | 60 |
| gccgggcctc | cgaggctcct | gctgctgccc | ctgcttctgg | cgctggctcg | cggcctgcct | 120 |
| ggggccctgg | ctgcccaagg | taagagcttc | ccaggctctc | catggccaca | gctccggagc | 180 |
| tctccctgcc | ccatgagctc | agagccccca | gtctgagcca | cagcacagcc | cccaggaagc | 240 |
| gggtggggtg | ctgagcggcc | tccagtgtct | gaggactcat | ttaagagaag | gaaaaagggt | 300 |
| ggacccggtg | gggagtggcc | ggggctgtcc | aggcagggcc | gctgctttgg | gaggaagaag | 360 |
| cccacagtct | cggaacacga | ggacagcacc | tcccccaaca | ccacagccgg | tgcccagatc | 420 |
| tgctccatgc | cccgtaaggc | accgtgtctt | tggcgacatg | tcagccctgg | gctgtctcag | 480 |
| ggccccacca | tccccaccac | tgtcccctgc | agggaggaca | ttctctgtcc | ttctggccag | 540 |
| actgatggtg | acagcccagg | tcctcccaga | ggtgcagcag | tctccccact | gcacgactgt | 600 |
| ccccgtggga | gcctccgtca | acatcacctg | ctccaccagc | gggggcctgc | gtgggatcta | 660 |
| cctgaggcag | ctcgggccac | agcccaaga | catcatttac | tacgaggacg | gggtggtgcc | 720 |
| cactacggac | agacggttcc | ggggccgcat | cgacttctca | gggtcccagg | acaacctgac | 780 |
| tatcaccatg | caccgcctgc | agctgtcgga | cactggcacc | tacacctgcc | aggccatcac | 840 |
| ggaggtcaat | gtctacggct | ccggcaccct | ggtcctggtg | acagaggaac | agtcccaagg | 900 |
| atggcacaga | tgctcggacg | ccccaccaag | ggcctctgcc | ctccctgccc | caccgacagg | 960 |
| ctccgccctc | cctgacccgc | agacagcctc | tgccctccct | gacccgccag | cagcctctgc | 1020 |
| cctccctgcg | gccctggcgg | tgatctcctt | cctcctcggg | ctgggcctgg | gggtggcgtg | 1080 |
| tgtgctggcg | aggacacaga | taaagaaact | gtgctcgtgg | cgggataaga | attcggcggc | 1140 |
| atgtgtggtg | tacgaggaca | tgtcgcacag | ccgctgcaac | acgctgtcct | cccccaacca | 1200 |

```
gtaccagtga cccagtgggc ccctgcacgt cccgcctgtg gtccccccag caccttccct    1260
gccccaccat gccccccacc ctgccacacc cctcaccctg ctgtcctccc acggctgcag    1320
cagagtttga agggcccagc cgtgcccagc tccaagcaga cacacaggca gtggccaggc    1380
cccacggtgc ttctcagtgg acaatgatgc ctcctccggg aagccttccc tgcccagccc    1440
acgccgccac cgggaggaag cctgactgtc ctttggctgc atctcccgac catggccaag    1500
gagggctttt ctgtgggatg ggcctggcac gcggccctct cctgtcagtg ccggcccacc    1560
caccagcagg cccccaaccc ccaggcagcc cggcagagga cgggaggaga ccagtccccc    1620
acccagccgt accagaaata aaggcttctg tgcttc                              1656
```

<210> SEQ ID NO 2
<211> LENGTH: 240
<212> TYPE: PRT
<213> ORGANISM: Homo sapiens

<400> SEQUENCE: 2

```
Met Ala Gly Pro Pro Arg Leu Leu Leu Pro Leu Leu Ala Leu
  1               5                  10                  15

Ala Arg Gly Leu Pro Gly Ala Leu Ala Ala Gln Glu Val Gln Gln Ser
             20                  25                  30

Pro His Cys Thr Thr Val Pro Val Gly Ala Ser Val Asn Ile Thr Cys
         35                  40                  45

Ser Thr Ser Gly Gly Leu Arg Gly Ile Tyr Leu Arg Gln Leu Gly Pro
     50                  55                  60

Gln Pro Gln Asp Ile Ile Tyr Tyr Glu Asp Gly Val Val Pro Thr Thr
 65                  70                  75                  80

Asp Arg Arg Phe Arg Gly Arg Ile Asp Phe Ser Gly Ser Gln Asp Asn
                 85                  90                  95

Leu Thr Ile Thr Met His Arg Leu Gln Leu Ser Asp Thr Gly Thr Tyr
            100                 105                 110

Thr Cys Gln Ala Ile Thr Glu Val Asn Val Tyr Gly Ser Gly Thr Leu
        115                 120                 125

Val Leu Val Thr Glu Glu Gln Ser Gln Gly Trp His Arg Cys Ser Asp
    130                 135                 140

Ala Pro Pro Arg Ala Ser Ala Leu Pro Ala Pro Pro Thr Gly Ser Ala
145                 150                 155                 160

Leu Pro Asp Pro Gln Thr Ala Ser Ala Leu Pro Asp Pro Pro Ala Ala
                165                 170                 175

Ser Ala Leu Pro Ala Ala Leu Ala Val Ile Ser Phe Leu Leu Gly Leu
            180                 185                 190

Gly Leu Gly Val Ala Cys Val Leu Ala Arg Thr Gln Ile Lys Lys Leu
        195                 200                 205

Cys Ser Trp Arg Asp Lys Asn Ser Ala Ala Cys Val Val Tyr Glu Asp
    210                 215                 220

Met Ser His Ser Arg Cys Asn Thr Leu Ser Ser Pro Asn Gln Tyr Gln
225                 230                 235                 240
```

<210> SEQ ID NO 3
<211> LENGTH: 2000
<212> TYPE: DNA
<213> ORGANISM: Homo sapiens
<220> FEATURE:
<221> NAME/KEY: CDS
<222> LOCATION: (119)..(865)

<400> SEQUENCE: 3

-continued

| | |
|---|---|
| attttcctgg ggctccgggg cgcggagaag ctgcatccca gaggagcgcg tccaggagcg | 60 |
| gacccgggag tgtttcaaga gccagtgaca aggaccaggg gcccaagtcc caccagcc | 118 |

| atg cag acc tgc ccc ctg gca ttc cct ggc cac gtt tcc cag gcc ctt | 166 |
|---|---|
| Met Gln Thr Cys Pro Leu Ala Phe Pro Gly His Val Ser Gln Ala Leu | |
| 1               5                   10                  15     | |

| ggg acc ctc ctg ttt ttg gct gcc tcc ttg agt gct cag aat gaa ggc | 214 |
|---|---|
| Gly Thr Leu Leu Phe Leu Ala Ala Ser Leu Ser Ala Gln Asn Glu Gly | |
|                 20                  25                  30     | |

| tgg gac agc ccc atc tgc aca gag ggg gta gtc tct gtg tct tgg ggc | 262 |
|---|---|
| Trp Asp Ser Pro Ile Cys Thr Glu Gly Val Val Ser Val Ser Trp Gly | |
|             35                  40                  45         | |

| gag aac acc gtc atg tcc tgc aac atc tcc aac gcc ttc tcc cat gtc | 310 |
|---|---|
| Glu Asn Thr Val Met Ser Cys Asn Ile Ser Asn Ala Phe Ser His Val | |
| 50                  55                  60                     | |

| aac atc aag ctg cgt gcc cac ggg cag gag agc gcc atc ttc aat gag | 358 |
|---|---|
| Asn Ile Lys Leu Arg Ala His Gly Gln Glu Ser Ala Ile Phe Asn Glu | |
| 65                  70                  75                  80 | |

| gtg gct cca ggc tac ttc tcc cgg gac ggc tgg cag ctc cag gtt cag | 406 |
|---|---|
| Val Ala Pro Gly Tyr Phe Ser Arg Asp Gly Trp Gln Leu Gln Val Gln | |
|                 85                  90                  95     | |

| gga ggc gtg gca cag ctg gtg atc aaa ggc gcc cgg gac tcc cat gct | 454 |
|---|---|
| Gly Gly Val Ala Gln Leu Val Ile Lys Gly Ala Arg Asp Ser His Ala | |
|                 100                 105                 110    | |

| ggg ctg tac atg tgg cac ctc gtg gga cac cag aga aat aac aga caa | 502 |
|---|---|
| Gly Leu Tyr Met Trp His Leu Val Gly His Gln Arg Asn Asn Arg Gln | |
|                 115                 120                 125    | |

| gtc acg ctg gag gtt tca ggt gca gaa ccc cag tcc gcc cct gac act | 550 |
|---|---|
| Val Thr Leu Glu Val Ser Gly Ala Glu Pro Gln Ser Ala Pro Asp Thr | |
| 130                 135                 140                    | |

| ggg ttc tgg cct gtg cca gcg gtg gtc act gct gtc ttc atc ctc ttg | 598 |
|---|---|
| Gly Phe Trp Pro Val Pro Ala Val Val Thr Ala Val Phe Ile Leu Leu | |
| 145                 150                 155                 160| |

| gtc gct ctg gtc atg ttc gcc tgg tac agg tgc cgc tgt tcc cag caa | 646 |
|---|---|
| Val Ala Leu Val Met Phe Ala Trp Tyr Arg Cys Arg Cys Ser Gln Gln | |
|                 165                 170                 175    | |

| cgc cgg gag aag aag ttc ttc ctc cta gaa ccc cag atg aag gtc gca | 694 |
|---|---|
| Arg Arg Glu Lys Lys Phe Phe Leu Leu Glu Pro Gln Met Lys Val Ala | |
|                 180                 185                 190    | |

| gcc ctc aga gcg gga gcc cag cag ggc ctg agc aga gcc tcc gct gaa | 742 |
|---|---|
| Ala Leu Arg Ala Gly Ala Gln Gln Gly Leu Ser Arg Ala Ser Ala Glu | |
|                 195                 200                 205    | |

| ctg tgg acc cca gac tcc gag ccc acc cca agg ccg ctg gca ctg gtg | 790 |
|---|---|
| Leu Trp Thr Pro Asp Ser Glu Pro Thr Pro Arg Pro Leu Ala Leu Val | |
| 210                 215                 220                    | |

| ttc aaa ccc tca cca ctt gga gcc ctg gag ctg ctg tcc ccc caa ccc | 838 |
|---|---|
| Phe Lys Pro Ser Pro Leu Gly Ala Leu Glu Leu Leu Ser Pro Gln Pro | |
| 225                 230                 235                 240| |

| ttg ttt cca tat gcc gca gac cca tag ccgcctgcaa ggcagagagg | 885 |
|---|---|
| Leu Phe Pro Tyr Ala Ala Asp Pro | |
|                 245             | |

| | |
|---|---|
| acacaggaga gccagccctg agtgccgacc ttgggtggcg gggcctgggt ctctcgtccc | 945 |
| acccggaggg cacagacacc ggcttgcttg gcaggctggg cctctgtgtc acccactcct | 1005 |
| gggtgcgtgc agacccttcc cctccacccc ccaggtcttc caagctctgc ttcctcagtt | 1065 |
| tccaaaatgg aaccacctca cctccgcagc acccgactta ccaggacgca tgcccctccc | 1125 |
| tctgccctca tcaaacccac agacccggac tcccttcctg ccaccccagg ctggtccggc | 1185 |

-continued

```
cccaggtgtg gggtccgctc tctccactcc cagggctccg cgcccaagtg aggggccccc    1245
tgccggagcc tcagacacac tggagttcag ggctgggggg gccttggcac atacctgtcc    1305
cttggctatg agcaggcttt gggggcccct ccgcggcagc cccggggggcc gaggtagggt    1365 ctgggggctt agaggctggg atggctcctg gccccaccgc caggggggcaa gcgcaggccg    1425 ggctggagg cggcggcggc ggctcgggct gggggtcag gtggacgctg cctccggggc      1485
tggtcgcgca tccctcagtc cctcggccac ccggggggtcg ctccctcgtg cccaccgcac   1545
ctgccgagcc tctttggacc cagatctgtt catgcttttg tcttcgtcac tgcggcgggg    1605 cccttttgatg tcttcatctg tatggggtgg aaaaatcacc gggaatcccc cttcagttct   1665
ttgaaaaagt tccatgactc gaatatctga atgaagaaa acaaaccgac tcacaaacct    1725
ccaagtagct ccaaatgcaa tttttaaat ggaaaacaaa aatctgaaag aaacgtcttt    1785
agtggcttta agccccaaaa cgtccctaag gcgtcctcga gatgaagacg ggggggagcc    1845
cccagccagg tggagacccc gcaggacgcg cggcgcccg gtgaccgagg cctcgcacag     1905
ccggccgccc tgagggtcgg gccggagcca gggtccaaga ggggcgcgtt tgtgtctcgg    1965
gttaaaataa ggttccgtcc gcgtgctggg tcaga                                2000
```

<210> SEQ ID NO 4
<211> LENGTH: 248
<212> TYPE: PRT
<213> ORGANISM: Homo sapiens

<400> SEQUENCE: 4

```
Met Gln Thr Cys Pro Leu Ala Phe Pro Gly His Val Ser Gln Ala Leu
 1               5                  10                  15

Gly Thr Leu Leu Phe Leu Ala Ala Ser Leu Ser Ala Gln Asn Glu Gly
                20                  25                  30

Trp Asp Ser Pro Ile Cys Thr Glu Gly Val Val Ser Val Ser Trp Gly
            35                  40                  45

Glu Asn Thr Val Met Ser Cys Asn Ile Ser Asn Ala Phe Ser His Val
        50                  55                  60

Asn Ile Lys Leu Arg Ala His Gly Gln Glu Ser Ala Ile Phe Asn Glu
    65                  70                  75                  80

Val Ala Pro Gly Tyr Phe Ser Arg Asp Gly Trp Gln Leu Gln Val Gln
                85                  90                  95

Gly Gly Val Ala Gln Leu Val Ile Lys Gly Ala Arg Asp Ser His Ala
                100                 105                 110

Gly Leu Tyr Met Trp His Leu Val Gly His Gln Arg Asn Asn Arg Gln
            115                 120                 125

Val Thr Leu Glu Val Ser Gly Ala Glu Pro Gln Ser Ala Pro Asp Thr
        130                 135                 140

Gly Phe Trp Pro Val Pro Ala Val Val Thr Ala Val Phe Ile Leu Leu
145                 150                 155                 160

Val Ala Leu Val Met Phe Ala Trp Tyr Arg Cys Arg Cys Ser Gln Gln
                165                 170                 175

Arg Arg Glu Lys Lys Phe Phe Leu Glu Pro Gln Met Lys Val Ala
            180                 185                 190

Ala Leu Arg Ala Gly Ala Gln Gln Gly Leu Ser Arg Ala Ser Ala Glu
        195                 200                 205

Leu Trp Thr Pro Asp Ser Glu Pro Thr Pro Arg Pro Leu Ala Leu Val
    210                 215                 220

Phe Lys Pro Ser Pro Leu Gly Ala Leu Glu Leu Leu Ser Pro Gln Pro
```

-continued

```
                225                 230                 235                 240

Leu Phe Pro Tyr Ala Ala Asp Pro
                245
```

<210> SEQ ID NO 5
<211> LENGTH: 978
<212> TYPE: DNA
<213> ORGANISM: Mus sp.

<400> SEQUENCE: 5

| | | | | |
|---|---|---|---|---|
| tgtgttgtag ccagagtggc tgatttggct cagatcacct ggatttgggc gtcatgactc | 60 |
| agcaggcagt gctggctttg ctgcttacac tggccggaat cctgcctggc cccctggatg | 120 |
| cccaagacgt acaccagtcc ccccgactca cgattgcctc tgagggggat tctgtcaaca | 180 |
| tcacctgctc tacaagaggg cacctggaag ggatcttaat gaagaagatc tggcctcagg | 240 |
| cttacaatgt gatttacttt gaagaccggc aggagcccac agtagacagg accttctcag | 300 |
| gccgaattaa tttctctggt tcccagaaga acctgaccat caccataagc tccctccagc | 360 |
| tggcagacac tggagactac acctgcgagg ctgtcaggaa agtcagtgcc cgtggcttgt | 420 |
| tcaccacggt tgtggtgaaa gaaaaatcat cccaagaagc atacagatcc caggaacctc | 480 |
| tgcagacatc attttccttc ccagctgcca ttgctgtagg cttcttcttc accgggctgc | 540 |
| tccttggggt ggtgtgcagc atgctgagga agatacagat caagaaactg tgtgcctcag | 600 |
| ggattaagga atctccgtgc gtagtgtatg aagacatgtc ctacagcaac cgcaagacgc | 660 |
| catgcatccc caaccagtac cagtgaaccc ctctgcctgc agtcccccgt gccttgtttc | 720 |
| agcagagctt acagcagtcc tgctggcccc cacaccccgc ccaactcccc agcactcttc | 780 |
| ctgtggtact caaattcccc cttggtgctt ctgggtgggt gggattcctc ctctgtaagc | 840 |
| tcccccacag ggctctgcaa tctgtcacca accctagcca ggtaccctga catcagaaac | 900 |
| aaagcttggg ggtggggagg tacctgcctt ggagccgcct ggccaggaaa aattaaataa | 960 |
| acacacaaat acattaac | 978 |

<210> SEQ ID NO 6
<211> LENGTH: 210
<212> TYPE: PRT
<213> ORGANISM: Mus sp.

<400> SEQUENCE: 6

```
Met Thr Gln Gln Ala Val Leu Ala Leu Leu Thr Leu Ala Gly Ile
  1               5                  10                  15

Leu Pro Gly Pro Leu Asp Ala Gln Asp Val His Gln Ser Pro Arg Leu
                 20                  25                  30

Thr Ile Ala Ser Glu Gly Asp Ser Val Asn Ile Thr Cys Ser Thr Arg
             35                  40                  45

Gly His Leu Glu Gly Ile Leu Met Lys Lys Ile Trp Pro Gln Ala Tyr
         50                  55                  60

Asn Val Ile Tyr Leu Glu Asp Arg Gln Glu Pro Thr Val Asp Arg Thr
 65                  70                  75                  80

Phe Ser Gly Arg Ile Asn Phe Ser Gly Ser Gln Lys Asn Leu Thr Ile
                 85                  90                  95

Thr Ile Ser Ser Leu Gln Leu Ala Asp Thr Gly Asp Tyr Thr Cys Glu
            100                 105                 110

Ala Val Arg Lys Val Ser Ala Arg Gly Leu Phe Thr Thr Val Val Val
        115                 120                 125
```

-continued

```
Lys Glu Lys Ser Ser Gln Glu Ala Tyr Arg Ser Gln Glu Pro Leu Gln
    130                 135                 140

Thr Ser Phe Ser Phe Pro Ala Ala Ile Ala Val Gly Phe Phe Thr
145                 150                 155                 160

Gly Leu Leu Leu Gly Val Val Cys Ser Met Leu Arg Lys Ile Gln Ile
                165                 170                 175

Lys Lys Leu Cys Ala Ser Gly Ile Lys Glu Ser Pro Cys Val Val Tyr
            180                 185                 190

Glu Asp Met Ser Tyr Ser Asn Arg Lys Thr Pro Cys Ile Pro Asn Gln
        195                 200                 205

Tyr Gln
    210

<210> SEQ ID NO 7
<211> LENGTH: 1112
<212> TYPE: DNA
<213> ORGANISM: Mus sp.
<220> FEATURE:
<221> NAME/KEY: CDS
<222> LOCATION: (135)..(773)

<400> SEQUENCE: 7
ggatccttca gagaacagag cattctttct tgtcatctga tcatggtgtc caacaacaac      60
aacaacaaca acaacaacaa caaaagacac tgaccagaac aattgtcttc tgaggcccat     120
cctaggaatg agcc atg ctg gcc tac tct gta aca tcc tct ggc ctg ttt       170
              Met Leu Ala Tyr Ser Val Thr Ser Ser Gly Leu Phe
                1               5                  10 ccc aga atg ctc tgg gcc ctc ctt cta ctg gcg gcc tcc ctg aat gcc       218
Pro Arg Met Leu Trp Ala Leu Leu Leu Leu Ala Ala Ser Leu Asn Ala
         15                  20                  25 cat aac gat gtc tgg gac gaa cct tgt tgc act gag cat gaa gta tct       266
His Asn Asp Val Trp Asp Glu Pro Cys Cys Thr Glu His Glu Val Ser
     30                  35                  40 gta aac aga ggc agc cgt gtg gtg atg gcc tgt aat atc tcc aac aat       314
Val Asn Arg Gly Ser Arg Val Val Met Ala Cys Asn Ile Ser Asn Asn
 45                  50                  55                  60 ctc aga gac gtc acc att gag ttg gtt acc agt gaa aag act agc atc       362
Leu Arg Asp Val Thr Ile Glu Leu Val Thr Ser Glu Lys Thr Ser Ile
                 65                  70                  75 atc ttc aat cat acg cct cca gga aac tac tct aag gat tca tgg cag       410
Ile Phe Asn His Thr Pro Pro Gly Asn Tyr Ser Lys Asp Ser Trp Gln
             80                  85                  90 ctt cat att caa gga gtc cag gcc cag ctg gtg atc aca gat gct cag       458
Leu His Ile Gln Gly Val Gln Ala Gln Leu Val Ile Thr Asp Ala Gln
         95                 100                 105 gac aaa cac tca ggg aac tac tcc tgg aag ctg cat gga ttc cag gca       506
Asp Lys His Ser Gly Asn Tyr Ser Trp Lys Leu His Gly Phe Gln Ala
    110                 115                 120 gag ttc aaa aac ttc aac ctg act gtt aat gcc gca gac aga cag aag       554
Glu Phe Lys Asn Phe Asn Leu Thr Val Asn Ala Ala Asp Arg Gln Lys
125                 130                 135                 140 aca gag gac ttg cca gtc act aag gtc cct gat aag ccc cca act gca       602
Thr Glu Asp Leu Pro Val Thr Lys Val Pro Asp Lys Pro Pro Thr Ala
                145                 150                 155 gtg cgg aca gaa gtt atc atc atc atc gcc att gct acc acc atc atc       650
Val Arg Thr Glu Val Ile Ile Ile Ile Ala Ile Ala Thr Thr Ile Ile
            160                 165                 170 atc aca gga atc ggt gta ttc gtt tgg tac aag caa ttc cct gta gct       698
Ile Thr Gly Ile Gly Val Phe Val Trp Tyr Lys Gln Phe Pro Val Ala
```

-continued

```
                   175                 180                 185
cca cag ata caa atg tca gta cct tgt ctg att cat ggg tct cct ggt    746
Pro Gln Ile Gln Met Ser Val Pro Cys Leu Ile His Gly Ser Pro Gly
    190                 195                 200 atc ccc tac ctg aca ctg ccc ccc taa agtctcccaa ttcctgcctc          793
Ile Pro Tyr Leu Thr Leu Pro Pro
205                 210 aaaagatact caagggacct tagtagctcc aaacatcagg ctacagagaa cctcacctgg  853
ctatggctga caatccaagc cctgattgac aagatcacag gaactctctg tctcccaagc  913
cctcattttg accttgggac aggtagacgt cagaatgggg tctgtactcc tcaggttcct  973
cccaagactc caggacaatt tgcactgagg acggcactgt ggttttttaac tgaggatacc 1033 ctggaagttg tctgaacccc tcctgtacat caaagtattt cagagtaaaa aaaaaaaaa  1093 aaaaaaaaaa aaaaaaaa                                                1112
```

<210> SEQ ID NO 8
<211> LENGTH: 212
<212> TYPE: PRT
<213> ORGANISM: Mus sp.

<400> SEQUENCE: 8

```
Met Leu Ala Tyr Ser Val Thr Ser Ser Gly Leu Phe Pro Arg Met Leu
 1               5                  10                  15

Trp Ala Leu Leu Leu Leu Ala Ala Ser Leu Asn Ala His Asn Asp Val
                20                  25                  30

Trp Asp Glu Pro Cys Cys Thr Glu His Glu Val Ser Val Asn Arg Gly
            35                  40                  45

Ser Arg Val Val Met Ala Cys Asn Ile Ser Asn Asn Leu Arg Asp Val
    50                  55                  60

Thr Ile Glu Leu Val Thr Ser Glu Lys Thr Ser Ile Ile Phe Asn His
65                  70                  75                  80

Thr Pro Pro Gly Asn Tyr Ser Lys Asp Ser Trp Gln Leu His Ile Gln
                85                  90                  95

Gly Val Gln Ala Gln Leu Val Ile Thr Asp Ala Gln Asp Lys His Ser
            100                 105                 110

Gly Asn Tyr Ser Trp Lys Leu His Gly Phe Gln Ala Glu Phe Lys Asn
        115                 120                 125

Phe Asn Leu Thr Val Asn Ala Ala Asp Arg Gln Lys Thr Glu Asp Leu
    130                 135                 140

Pro Val Thr Lys Val Pro Asp Lys Pro Pro Thr Ala Val Arg Thr Glu
145                 150                 155                 160

Val Ile Ile Ile Ile Ala Ile Ala Thr Thr Ile Ile Thr Gly Ile
                165                 170                 175

Gly Val Phe Val Trp Tyr Lys Gln Phe Pro Val Ala Pro Gln Ile Gln
            180                 185                 190

Met Ser Val Pro Cys Leu Ile His Gly Ser Pro Gly Ile Pro Tyr Leu
        195                 200                 205

Thr Leu Pro Pro
    210
```

LIGAND FOR CD7 AND METHODS FOR USE THEREOF

RELATED APPLICATION

This application is a continuation in part of International Patent Application No. PCT/US00/14612, filed May 26, 2000, which claims priority to U.S. Provisional Application Serial No. 60/136,450, filed May 28, 1999, now abandoned, the disclosures of which are incorporated by reference herein.

FIELD OF THE INVENTION

This invention relates generally to ligands for CD7 and uses thereof to treat diseases, isolated polynucleotide molecules encoding such ligands, purified ligands, and methods of screening for molecules that affect the interaction between CD7 and its cognate ligand K12.

BACKGROUND OF THE INVENTION

Cellular change is often triggered by the binding of an extrinsic element, such as a ligand, to the extracellular domain of a receptor protein. This binding can result in cellular changes by activating and controlling intracellular signaling cascades and cell regulatory mechanisms. As such, understanding the binding interaction between the ligand and its receptor protein can be of great interest to the scientific community. A greater understanding of the interaction would enable one skilled in the art to modulate the resulting signaling cascade governed by the ligand/receptor interaction by selecting agents for co-stimulation or inhibition of the binding of the ligand to its receptor. Furthermore, in the instances of bi-directional or reverse signaling, the interaction would not only activate the signaling cascade of the receptor but would also trigger a signaling cascade in a cell bearing the ligand (Wiley et al., J. of Immun., 3235–39 (1996)). Thus, understanding the interaction between a receptor and ligand can lead to therapeutic treatments involving the inhibition or enhancement of either one or both of the receptor activity or ligand activity.

CD7 is a 40 kDa protein found primarily on hematopoietic cells. CD7 is expressed on mature T and natural killer (NK cells), as well as on progenitors of T, B, NK, and myeloid cells (Aruffo, Embo J. 6:3313 (1987); Yoshikawa, Immunogenetics 33:352 (1991); Yoshikawa, Immunogenetics 37:114 (1993); Yoshikawa, Immunogenetics 41:159 (1995)) and on intestinal intraepithelial lymphocytes (Spencer, Gut 30:339 (1989); Eiras, Cytometry 34:95 (1998)). In addition, CD7 is thought to be a marker for one of the earliest stages of T cell development (reviewed in Barcena, Leuk Lymphoma 17:1 (1995) and Haynes, Semin Immunol 2:67 (1990)).

Although all of the functions of the CD7 protein in the immune system are unknown, signaling through CD7 has been reported using anti-CD7 antibodies (Carrera, J.Immunol 141:1919 (1988); Rabinowich, J.Immunol Vol. 153:3504 (1994)), indicating that the cytoplasmic domain of CD7 must contain some signal tranducing elements or that it complexes with a protein containing such elements. Recombinant soluble CD7 also inhibits antigenic- and alloantigenic-induced T cell proliferation (Leta, Cell Immunol 165:101 (1995)).

Previous efforts to identify a cognate for CD7 have not been successful, although a putative ligand has reportedly been detected in serum (Leta, Cell Immunol 173:15 (1996)). The extracellular domain of CD7, expressed by either mammalian or insect cells, has been shown to interact with some specificity with Con A (Id.). This interaction is at least partly mediated through carbohydrate residues on CD7 since treatment of the extracellular domain of CD7 with glycosidases specifically reduces binding of Con A to CD7.

A recent study used model systems to investigate whether CD7 deficient mice are resistant to LPS-induced shock. According to the study, CD7 deficient mice were totally resistant to low-dose LPS-induced shock syndrome and were partially resistant to high-dose LPS-induced shock syndrome. Thus, this data indicates that CD7 is involved in the LPS-induced shock pathway (Sempowski et al., J. Exp. Med. 189, 1011–1016 (1999)).

Given the role CD7 plays in signal transduction (including its mediation of the LPS-induced shock pathway), there is a need in the art for the identification and understanding of the interaction of CD7 with its cognate ligand or binding partner. Further, there is a need for the development of assays and therapeutic methods using the interaction between CD7 and its binding ligand.

The K12 gene (also known as SECTM1) was originally identified (Slentz-Kesler, Genomics 47:327(1998)) as being directly 5' of the locus encoding the human CD7 gene on human chromosome 17 (Osada, Cytogenet Cell Genet (1988)). The 3' end of the K12 gene is about 5 kb upstream of the start of the human CD7 gene, and both genes are transcribed in the same direction (Slentz-Kesler, 1998). The K12 gene encodes a transmembrane protein with two short regions in the extracellular domain with weak similarity to Ig-like domains. Both membrane-bound (localized to the Golgi apparatus) and secreted forms of the protein were observed (Id.). In humans, the protein is primarily expressed in spleen, prostate, testis, small intestine, and in peripheral blood leukocytes (Id). However, no known function for the K12 protein has yet been identified.

SUMMARY OF THE INVENTION

The invention is based, in part, on the discovery that the cognate for the K12 protein is CD7. Thus, K12 is the previously unknown ligand or binding partner for CD7. Accordingly, an aspect of the invention is the use of the K12 protein, and polynucleotides encoding the same, in methods of modulating CD7 and K12 signaling events, and in treating diseases. The invention also provides isolated polynucleotide molecules encoding novel K12 proteins, and the recombinant and/or purified K12 polypeptides encoded by such polynucleotides.

Other aspects of the invention include methods of screening for compounds, which are referred to as "test compounds" or "candidate molecules" that affect the K12/CD7 interaction. In one aspect, the method comprises the steps of forming a composition comprising a CD7 protein, a K12 protein, and the test compound; assaying for the level of interaction of the CD7 protein and the K12 protein; and comparing the level obtained in the presence of the test compound to that obtained in the absence of the test compound, such that if the level obtained differs, a compound that affects the interaction of the CD7 protein and the K12 protein is identified. At least one of the CD7 protein and the K12 protein can be labeled with a detectable moiety. Preferred test compounds are small organic molecules, antibodies, and small peptides. One of the CD7 protein or the K12 protein can be soluble, and the other can be bound, although alternative assay formats are possible and well known. The test compound can be added to the composition after addition of the CD7 protein and the K12 protein, before both proteins are added, or after one protein is added and before the other is added.

In another aspect, the screening methods of the invention comprise forming a composition comprising the test compound, the K12 protein and cells expressing CD7; determining the level of biological activity of the K12 protein in the composition; and comparing the level of biological activity with that which occurs in the absence of test compound, wherein a difference in the level of biological activity indicates that the test compound affects the biological activity of a K12 protein. Biological activity of K12 can be assayed in any number of ways, for example, by determining the phosphorylation state of intracellular proteins, by determining the activation of NK cells and by determining the production of interferon gamma and/or GM-CSF. In a related aspect, the cells express K12 and soluble CD7, or cells expressing CD7, is used.

The present invention also provides a screening method for identifying candidate molecules that enhance or inhibit the interaction between CD7 and K12, or that prevent or inhibit dissociation of a complex formed by CD7 and K12. This screening method involves contacting a mixture of cells which express CD7 and cells which express K12 with a candidate molecule, measuring cellular responses, and detecting the ability of the candidate molecule to inhibit or enhance the interaction between CD7 and K12 or inhibit the dissociation of the complex formed by CD7 and K12. Successful inhibition indicates that the candidate molecule is an antagonist. Increased activation of CD7 or K12 indicates that the candidate molecule is an agonist.

In another aspect, the invention provides antagonists and agonists of the interaction between CD7 and K12. In yet a further aspect, the invention provides for a therapeutic use of agonists and antagonists of the interaction between CD7 and K12 in the treatment of diseases modulated by CD7 and/or K12. In still a further aspect, the invention provides for a therapeutic use of K12 in the treatment of disease modulated by CD7. In yet still a further aspect, the invention provides for a therapeutic use of CD7 in the treatment of disease modulated by K12.

BRIEF DESCRIPTION OF THE SEQUENCES

SEQ ID NO:1 is the cDNA sequence of human CD7.

SEQ ID NO:2 is the amino acid sequence of human CD7.

SEQ ID NO:3 is the nucleic acid sequence of human K12.

SEQ ID NO:4 is the amino acid sequence of human K12.

SEQ ID NO:5 is the cDNA sequence of murine CD7.

SEQ ID NO:6 is the amino acid sequence of murine CD7.

SEQ ID NO:7 is the nucleic acid sequence of murine K12.

SEQ ID NO:8 is the amino acid sequence of murine K12.

BRIEF DESCRIPTION OF THE DRAWINGS

FIG. 1: Sequence comparison of the human K12 protein (SEQ ID NO:4) and its mouse homologue (SEQ ID NO:8). Protein sequences were compared using the GCG program GAP. The arrow indicates the predicted signal peptide cleavage site in both the human and mouse proteins. Potential N-linked glycosylation sites are underlined, and the core transmembrane regions (predicted by the TRANSMEMBRANE program) as well as conserved cysteine residues are boxed.

FIG. 2: Effect of K12 poly-His Flag, K12/hu IgG1 Fc fusion protein, soluble CD7 poly-His flag, soluble CD4 and a negative control on inhibiting syncytia. The graph demonstrates the effect of K12 poly-His Flag, K12/hu IgG Fc fusion protein, CD7, CD4 and a negative control in the assay described in Example 10 on syncytia induction by HIV-1 MN at various concentrations.

DETAILED DESCRIPTION OF THE INVENTION

The invention is based, in part, on the discovery that the ligand for CD7 is K12. In brief, a soluble labeled version of a human K12 extracellular domain fused to the Fc portion of human IgG1 was recombinantly produced and found, using flow cytometry experiments, to bind at high levels to both human T and NK cells. This K12-Fc fusion was used to clone the cognate binding protein from a human T cell cDNA expression library. Sequencing of two independent clones revealed that the cDNAs encoded CD7. Subsequent experiments verified that CD7 was indeed the cognate binding partner for K12.

The term "CD7" includes the protein and its variants disclosed in U.S. Pat. No. 5,506,126, and includes fragments of CD7, soluble forms of CD7 and homologous analogs. Full length CD7 comprises an extracellular domain, a transmembrane domain, and a cytoplasmic domain. The full length cDNA sequence of human CD7 is provided in SEQ ID NO:1 with the corresponding amino acid sequence provided in SEQ ID NO:2, and the full length cDNA sequence of murine CD7 is provided in SEQ ID NO:5 with the corresponding amino acid sequence provided in SEQ ID NO:6.

"Fragments" of CD7 encompass truncated amino acid sequences of the CD7 protein that retain the biological ability to bind to K12. An example of such a fragment is the extracellular domain of CD7.

"Soluble CD7" includes truncated proteins that lack a functional transmembrane domain of the protein but retain the biological activity of binding to K12. The soluble, extracellular domain can be used to inhibit cellular activation.

"Homologous analogs" of CD7 include proteins encoded by nucleic acids that are at least about 30% identical to SEQ ID NO:1, yet which still retain the biological activity of binding to K12. Also contemplated by the term are embodiments in which the homologous analog of CD7 is encoded by a nucleic acid molecule that is at least about 40% identical, preferably at least about 50% identical, more preferably at least about 60% identical, yet more preferably at least about 70%, even more preferably at least about 80% identical, still more preferably at least about 90% identical, and most preferably at least about 95% identical to SEQ ID NO:1, wherein the encoded homologous analog of CD7 retains the biological activity of binding to a K12 protein.

Further included are proteins which are at least about 35% similar, preferably at least about 55% similar, more preferably at least about 70%, yet more preferably at least about 85% similar, even more preferably at least about 95% similar, and most preferably at least about 99% similar to the CD7 protein polypeptide as described in SEQ ID NO:2, and that maintain a binding affinity to a K12 protein. By "similar" in this context is meant that the variant protein contains either the same amino acid residue at a particular relative position, or a conservative amino acid substitution at that residue position. Conserved amino acid substitutions are made on the basis of similarity in polarity, charge, solubility, hydrophobicity, hydrophilicity, and/or the amphipathic nature of the residues involved. For example, nonpolar (hydrophobic) amino acids which can be substituted for each other include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Still further included are all substantially homologous analogs and allelic variations.

An example of a homologous analog of CD7 is a murine homologue. The human CD7 protein differs from its mouse homologue in that it contains a "spacer" region consisting of 4 tandem repeats of 9 amino acids (XPPXASALP) in the area proximal to the membrane spanning part of the protein (Yoshikawa, *Immunogenetics* 37:114 (1993)). Targeted disruption of the CD7 gene in mice has been achieved by several groups (Lee, *J.Immunol.* 160:5749 (1998)); Bonilla, *Int. Immunol.* 9:1875 (1997)). One group found no demonstrable effect on either the function or subsets of lymphocytes, and no effect on NK cell cytotoxicity (Bonilla, 1997). However, the second group did note a transient increase in thymocyte numbers at 3 months and an alteration in antigen specific CTL effector activity (Lee, 1998.) When examined, expression of the human CD7 gene in transgenic mice had no effect on mouse thymopoiesis, even though the gene was expressed in T cells and was induced during T cell activation (Schanberg, *J. Immunol.* 155:2407(1995)). This result can now be explained by the fact that mouse K12-Fc cannot bind to human CD7 (see Example 5, below). Thus, human CD7 does not substitute for mouse CD7 in a mouse model. In addition, present inventors have discovered that the murine homologue of CD7 binds to the murine homologue of K12 but not its human counterpart (see below).

The percent identity and percent similarity can be determined by visual inspection and mathematical calculation. Alternatively, the percent identity of two nucleic acid molecules can be determined by comparing their sequences using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities), and the weighted comparison matrix of Gribskov and Burgess, *Nucl. Acids Res.* 14:6745, 1986, as described by Schwartz and Dayhoff, eds., *Atlas of Protein Sequence and Structure,* National Biomedical Research Foundation, pp. 353–358, 1979; (2) a penalty of 3.0 for each gap and an additional 0.10 penalty for each symbol in each gap; and (3) no penalty for end gaps. Other programs used by one skilled in the art of sequence comparison may also be used such as the BLAST program for both nucleotide and amino acid comparisons.

The term "K12" includes the protein as described above and as shown in FIG. 1, including fragments of K12 that retain the ability to bind to CD7. The full-length human K12 protein comprises a signal sequence (approximately amino acids 1–28 of SEQ ID NO:4) an extracellular domain sequence (approximately amino acids 29–145 of SEQ ID NO:4), a transmembrane domain sequence (approximately amino acids 146–167 of SEQ ID NO:4), and a cytoplasmic domain sequence (approximately amino acids 168–248 of SEQ ID NO:4). The skilled artisan will recognize that the above-described boundaries of such regions of the polypeptide are approximate. To illustrate, the boundaries of the signal peptide may differ from those described above. As a guideline, the boundaries may differ by about 1 to 4 residues on either side of the above-described boundaries. "Fragments" of K12 encompass truncated amino acids of the K12 protein that retain the biological ability to bind to CD7. An example of such a fragment is the extracellular domain of K12, which binds CD7. "Soluble K12" includes truncated proteins that lack a functional transmembrane domain of the protein but retain the biological activity of binding to CD7. Naturally occurring soluble forms of human K12 are fragments of the extracellular domain of approximately 19–22 Kd. Thus, soluble K12 molecules need not contain the entire above-described extracellular domain of K12, but can be truncated by 1 to 20 amino acids at the N terminus, and/or truncated by 1 to 20 amino acids at the C terminus, as long as they retain binding affinity for CD7. For example, soluble K12 proteins may comprise approximately amino acid residues 49 to 125 and 49 to 165 of SEQ ID NO: 4. Soluble forms of K12 can be fusion proteins. Fusion proteins are proteins covalently linked to heterologous amino acid sequences (i.e., amino acid sequences that are not naturally linked to the K12 protein). Particularly preferred fusion proteins contain heterologous amino acid sequences that promote aggregation of the extracellular domain of K12 into multimeric (e.g., dimer, trimer, tetramer, etc.) forms of the protein, and/or that facilitate purification and/or detection (e.g., Fc domains, leucine zipper domains and poly-His tags, to name just a few).

"Homologous analogs" of K12 include proteins encoded by nucleic acids that are at least about 30% identical to SEQ ID NO:3, yet which still retain the biological ability to bind to a CD7. Also contemplated by the term are embodiments in which the homologous analog of K12 is encoded by a nucleic acid molecule that is at least about 40% identical, preferably at least about 50% identical, more preferably at least about 60% identical, yet more preferably at least about 70%, even more preferably at least about 80% identical, still more preferably at least about 90% identical, and most preferably at least about 95% identical to SEQ ID NO:3, wherein the encoded homologous analog of K12 still retains the biological ability of binding to a CD7. Further included are proteins which are at least about 35% similar, preferably at least about 55% similar, more preferably at least about 70%, yet more preferably at least about 85% similar, even more preferably at least about 95% similar, and most preferably at least about 99% similar to the CD7 protein polypeptide as described in SEQ ID NO:4, and that maintain a binding affinity to a CD7 protein. Still further included are all substantially homologous analogs and allelic variations.

An example of a homologous analog of K12 is the murine homologue, which is capable of binding to the murine homologue of CD7. This novel polypeptide is described in SEQ ID NO:8. Encoded within the cDNA of the murine K12 homologue is a 212 amino acid transmembrane protein that overall shares 36% amino acid identity over its entire length with the human K12 protein (FIG. 1) and 44% amino acid identity over the extracellular regions. The full-length murine K12 protein comprises a signal sequence (approximately amino acids 1–28 of SEQ ID NO:8) an extracellular domain sequence (approximately amino acids 29–160 of SEQ ID NO:8), a transmembrane domain sequence (approximately amino acids 161–181 of SEQ ID NO:8), and a cytoplasmic domain sequence (approximately amino acids 182–212 of SEQ ID NO:8). As noted above, the above-described boundaries of such regions of the polypeptide are approximate and may differ from those described above by about 1 to 4 residues on either side of the above-described boundaries. Further, as noted above, the soluble extracellular domain can be truncated by 1 to 20 amino acids at the N terminus, and/or truncated by 1 to 20 amino acids at the C terminus, as long as it retains binding affinity for murine CD7.

As the murine K12 homologue was previously unknown, an aspect of the invention described herein is these novel K12 proteins, and polynucleotides encoding the same. In one embodiment, the invention provides an isolated polynucleotide molecule that encodes a soluble K12 protein, wherein the polynucleotide molecule or its complement hybridizes to nucleotides 279 to 554 of SEQ ID NO:7. In another aspect, the invention provides an isolated polynucleotide molecule that encodes an intracellular domain of a murine K12 protein, wherein the polynucleotide molecule or its complement hybridizes to nucleotides 677 to 770 of SEQ ID NO:7. Preferably, the polynucleotide hybridizes under conditions of moderate stringency, such as, for example, 50% formamide and 6×SSC, at 42° C. with washing conditions of 60° C., 0.5×SSC, 0.1% SDS. Even more preferably, the polynucleotide hybridizes under high stringency conditions, such as, for example, the hybridization conditions given above, but with washing at approximately 68° C., 0.2×SSC, 0.1% SDS. A preferred example is a polynucleotide molecule that encodes a protein comprising amino acid residues 49 to 140 of SEQ ID NO:8. The polynucleotides of the invention can be used to recombinantly produce the encoded proteins. Recombinantly produced proteins can be prepared in greater quantities and at increased purity over that of proteins isolated from a naturally occurring source. In addition, recombinant production of proteins can ensure that no undesirable contamination is present from, from example, pathogenic organisms such as viruses and bacteria.

The invention also encompasses host cells that contain the above polynucleotides, and host cells genetically engineered to express the polynucleotide molecules of the invention under the control of a heterologous promoter. Host cells can be bacterial, fungal, animal, or plant cells, but preferably are mammalian cells such as, for example, cells grown in culture. Vectors, including expression vectors, and processes for transforming or transfecting host cells with such vectors are well known in the art (see Sambrook et al., *Molecular Cloning: A Laboratory Manual,* 2ed. Vol. 1, pp. 1.101–104, Cold Spring Harbor Laboratory Press, (1989)). If the host cell contains an endogenous K12 gene, the host cells can also be induced to express, or express increased quantities, of the K12 gene product by the techniques of homologous recombination and gene activation (see U.S. Pat. No. 5,272,071).

The invention also encompasses the purified and/or recombinant proteins encoded by, inter alia, the above polynucleotides. Purified protein is protein that is substantially free of other cellular constituents (e.g., greater than 50%, preferably greater than 90%) of the protein in the composition is the desired protein). For example, the invention encompasses a protein that has the sequence of SEQ ID NO:8, or a protein that comprises amino acid residues 49 to 140 of SEQ ID NO:8 yet is soluble and binds to a CD7 protein, or a protein that comprises amino acid residues 182 to 212 of SEQ ID NO:8 (the intracellular domain of murine K12). The soluble forms of murine K12 that bind to CD7 can be used in the methods described herein. The intracellular domain of murine K12 protein is useful for screening for the specific intracellular targets of K12, and for determining the cellular machinery responsible for targeting of proteins, in general, to the Golgi apparatus (where K12 has been described by other groups as localizing) and/or the cell surface (where K12 was found to accumulate in the experiments described herein). For example, the intracellular domain likely contains a specific recognition signal for coated vesicle transport.

The term "CD7/K12 complex" refers to the protein unit formed by the binding interaction of CD7 to K12. The term "CD7/K12 fragment complex" includes the protein units formed in which at least one binding partner is either a fragment of CD7 or K12 (e.g. the binding interaction of a CD7 fragment to K12, CD7 to a K12 fragment, or a CD7 fragment to a K12 fragment) or a homologous analog of CD7 or K12. In one embodiment of the invention, the 36 amino acid "spacer" region (4 repeats of 9 amino acids (XPPXASALP) in the area proximal to the membrane spanning part of the protein) within the human CD7 protein was removed as an internal deletion. Human K12-Fc still bound to the truncated (HuCD7-TR) form of human CD7, though the level of binding was lower (approximately 10 fold lower) than that which was observed to the full length human CD7 protein. Thus, there are different affinities of human K12-Fc for the normal vs. truncated versions of human CD7 or differential cell surface expression of the normal vs. truncated CD7 proteins in the transfected cells. In addition, knowing that the cognate ligand for CD7 is K12, one skilled in the art can easily determine which soluble forms of the CD7 receptor can be used as antagonists of the cell associated CD7 receptor.

The term "biological activity" includes the binding of CD7 to K12 or fragments thereof and the biological effects that result therefrom. A K12 protein has the biological activity of binding to a CD7 protein if the binding affinity ($K_a$) of the complex formed between the K12 protein and the CD7 protein is within about 2 orders of magnitude of that of the complex formed between the naturally occurring CD7 and K12 proteins. In preliminary experiments, the $K_a$ of human K12-Fc for human CD7 was estimated to be in the range of $1 \times 10^8$ $M^{-1}$ on both Jurkat (a human T cell leukemia cell line) and KG-1 cells (a human myelogenous leukemia cell line). Because of the species specificity of the interaction between CD7 and K12, care should be taken to choose a K12 protein, or antagonist thereof, that is appropriate for the particular CD7/K12 pair that is to be modulated in the methods of the invention. The term "biological effects" includes the cellular changes or effects that result from interaction of a CD7 protein with a K12 protein. Therefore, when one refers to the "K12/CD7 interaction" it is understood to include K12/CD7 binding, K12/CD7 affinity, K12/CD7 avidity, K12/CD7 dissociation and resultant biological effects. Consequently, "assaying for the level of interaction of a CD7 protein and a K12 protein" involves measuring by various methods the modulation of K12/CD7 binding, K12/CD7 affinity, K12/CD7 avidity, K12/CD7 dissociation and resultant biological effects.

The interaction between CD7 and K12 is, at least in part, a protein—protein interaction. Protein-protein interactions can be observed and measured in binding assays using a variety of detection methodologies that include, but are not limited to, surface plasmon resonance (Biacore), radioimmune based assays, and fluorescence polarization binding assays. When performed in the presence of a test compound, the ability of the test compound to modulate (e.g., enhance or inhibit) the protein—protein binding affinity is measured.

CD7 and K12 are very similar in size (248 amino acids for human K12; 240 amino acids for human CD7) so neither fits the classical definition of a receptor, which is usually significantly larger than its ligand. Although one group reported that significant amounts of the full length, membrane-bound K12 do not accumulate on the cell surface (Slentz-Kesler, 1998), the instant invention demonstrates that membrane-bound K12 does accumulate on the cell surface, at least in transfected cells (see below). Human CD7-Fc bound to the surface of cells transfected with a full length human K12 cDNA, and mouse CD7-Fc bound to cells transfected with a full length mouse K12 cDNA. Therefore, the CD7 protein could trigger some signaling pathway in cells expressing K12 on the cell surface. Accordingly, soluble forms of CD7 could be used to trigger K12 signaling.

Knowing that K12 binds to CD7 indicates several uses for exploiting the interaction between CD7 and K12, the K12 protein, and/or molecules derived thereof. As stated above, signaling through CD7 has been reported using anti-CD7 antibodies.

Biological effects of K12/CD7 interaction have been reported in the literature. For example, antibody-induced ligation of CD7 on the surface of either T cells or NK cells lead to the phosphorylation of intracellular proteins in those cells (Rabinowich, *J. Immunol.* Vol. 153:3504 (1994)). Crosslinking of CD7 on T cells has been shown to increase adhesion of the cells to fibronectin, ICAM-1, and V-CAM1 (Shimizu, *J Exp Med* 175:577 (1992)), and cross-linking of CD7 on NK cells has been shown to induce adhesion to fibronectin (Rabinowich, *J. Immunol.* Vol. 152:517 (1994)). Triggering CD7 has also been shown to regulate the functional activity of beta 1 integrins on NK cells (Rabinowich, *J. Immunol.* Vol. 152:517 (1994)). The interaction between CD7 and anti-CD7 antibodies inhibits proliferation in allogeneic and autologous mixed lymphocyte reactions (Lazarovits, *Transplant Proc* 20:1253(1988)), stimulates NK cell proliferation, enhances the cytotoxicity of the cells, and induces interferon gamma production (Rabinowich, *J. Immunol.* Vol. 152:517 (1994)). Furthermore, the effects of the interaction between CD7 and anti-CD7 antibodies are not limited to T and NK cells as GM-CSF production by several myeloid cell lines is also stimulated (Hou, *Blood* 88:124 (1996)).

K12, including immobilized soluble forms of K12, also stimulates NK cell activation (see below). Accordingly, as a binding protein of CD7, K12 can have the same biological activities and effects on CD7-expressing cells as the agonistic anti-CD7 antibodies. Indeed, the use of soluble forms of K12 to stimulate the activity of CD7 has a number of advantages over the use of an antibody to CD7. For example, soluble forms of K12 can be less immunogenic than a heterologous antibody, and using K12 to stimulate CD7 will more closely mimic the biological events that normally activate CD7. Thus, the invention provides methods of inhibiting T cell proliferation and/or activating NK cell proliferation and/or inducing interferon gamma production in a mammal comprising administering to the mammal an effective amount of a soluble K12 protein. In a related aspect, the invention provides a method of stimulating the intracellular signaling of CD7 comprising contacting a cell that expresses CD7 with an effective amount of a recombinant K12 protein. A recombinant K12 protein is a protein that is produced using genetic engineering techniques such that it is essentially free of the contaminating proteins normally associated with the protein in its naturally occurring state, e.g., for human K12, other human proteins.

CD7 has been suggested to be involved in both HIV-1 infection and syncytia formation since anti-CD7 antibodies block both of these processes (Sato, *J. Immunol* 152:5142 (1994)). A K12 protein, preferably a soluble form of K12, can also be used to block HIV infection and syncytia formation. In fact, as shown herein below, soluble forms of K12 were able to block syncytia formation. Thus, soluble forms of K12 can be used to treat diseases caused by HIV-1, as well as other viruses whose transmission is mediated by CD7 and/or K12.

A monoclonal antibody directed against CD7 has also been shown to inhibit T cell proliferation in the allogeneic mixed lymphocyte reaction (Lazarovits, *Transplant Proc.* 20:1253 (1988)). This study has led to a clinical trial of an anti-CD7 antibody for the prophylaxis of kidney transplant rejection (Lazarovits, *J.Immunol* 150:5163 (1993)). K12, such as soluble K12 protein, could be used in a similar fashion.

K12 is involved in the LPS-induced shock pathway. As shown in Sempowski (1999), transgenic mice that do not express CD7 are resistant to LPS-induced shock. Thus the interaction between CD7 and K12 plays a role in the LPS-induced shock pathway and associated syndromes such as sepsis. Neutralizing antibodies to K12 can be used to block the interaction between K12 and CD7, prevent CD7 activation, and thus treat sepsis.

Since CD7 can be a marker for T cell leukemias (reviewed in Haynes, *Immunol Today* 10:87 (1989)), immunotoxins have been created by fusing anti-human CD7 monoclonal antibodies to toxins such as ricin (Frankel, *Leuk Lymphoma* 26:287 (1997); Pauza, *J.Immunol* 158:3259 (1997)) or saporin (Flavell, *Br J Cancer* 75:1035 (1997)). One can conjugate toxins to the extracellular domain of K12 as well; these conjugates can be less immunogenic than antibody-based conjugates and/or can have a longer half-life. Conjugation of the anti-CD7 antibodies with toxins may not even be required, since anti-CD7 antibodies alone have been effective anti-tumor agents in a xenografted human T cell ALL model (Baum, Br. *J. Haemotol.* 95:327(1996)). K12-Fc should have a similar effect in this model, and thus can be used against T cell leukemias.

Screening Assays

The interaction between CD7 and K12 can also be exploited in screening assays for identifying candidate molecules (also referred to as test compounds) that influence the interaction of CD7 and K12, which includes small molecules, antibodies, peptides, peptidomimetic, pharmaceuticals or pharmacologic compounds or drugs, toxins, natural products and/or chemical compounds. In addition, a test compound may comprise a nucleic acid segment containing a gene that express a protein that modulate the K12/CD7 interaction, as well as a vector (viral or non-viral) containing said gene. Specific screening methods are known in the art and many are extensively incorporated in high throughput test systems so that large numbers of test compounds can be screened within a short amount of time. The assays can be performed in a variety of formats, including protein—protein binding assays, biochemical screening assays, immunoassays, cell based assays, etc. These assay formats are well known in the art. The screening assays of the present invention are amenable to screening of chemical libraries and are suitable for the identification of small molecule drug candidates, antibodies, peptides, peptidomimetics, and the like. Chemical libraries include commercially available combinatorial chemistry compound libraries from companies such as, but not limited to, Sigma-Aldrich (St. Louis, Mo.), Arqule (Woburn, Mass.), Enzymed (Iowa City, Iowa), Maybridge Chemical Co.(Trevillett, Cornwall, UK), MDS Panlabs (Bothell, Wash.), Pharma-copeia (Princeton, N.J.), and Trega (San Diego, Calif.).

By observing the effect that candidate molecules have on the interaction between CD7 and K12 in various binding assays, on CD7/K12-mediated activity in biological function tests, and in cell based screens, molecules (i.e., test compounds) that are potential therapeutics because they can modulate the interaction between CD7 and K12 are identified. Such molecules can promote the biological activity of the CD7/K12 complex, prevent the formation of the CD7/K12 complex or inhibit dissociation of the CD7/K12 complex already formed. Molecules preventing the interaction of CD7 and K12, and hence the activation of CD7, can be useful as immunosuppressants or anti-inflammatory agents. Molecules that promote the interaction of CD7 and K12 can be useful when enhancement of the immune system is desired.

Moreover, combinations of screening assays can be used to find molecules that regulate the biological activity of CD7/K12 interactions. In using combinations of various assays to screen for test compounds, it is understood that any of the assays described herein may be used in any order and combination. For example, one embodiment may comprise first determining whether a test compound binds to CD7 or K12 or modulates the binding of CD7 and K12 to one another by using an assay that is amenable to high throughput screening. Test compounds identified in this manner are then added to a biological assay to determine biological effects. Molecules that bind and that have an agonistic or antagonistic effect on biologic activity will be useful in treating or preventing disease or conditions with which CD7 and K12 are implicated.

Generally, an antagonist will inhibit CD7/K12 binding and consequential biological activity by at least 30%; more preferably by at least 50%, and most preferably by at least 90%. Similarly, an agonist will enhance the CD7/K12 binding and consequential biological activity by at least 20%; more preferably by at least 30%, and most preferably by at least 50%. Those of skill in the art will recognize that agonists and/or antagonists with different levels of agonism or antagonism respectively may be useful for different applications (i.e., for treatment of different disease states).

Small molecule agonists and antagonists are usually less than 10K molecular weight and may possess a number of physicochemical and pharmacological properties which enhance cell penetration, resist degradation and prolong their physiological half-lives (Gibbs, J., Pharmaceutical Research in Molecular Oncology, Cell, Vol. 79 (1994)). Antibodies may be agonistic or antagonistic and include intact molecules as well as fragments such as Fab and F(ab')2 fragments, as well as recombinant molecules derived therefrom (including antibodies expressed on phage, intrabodies, single chain antibodies such as scFv and other molecules derived from immunoglobulins that are known in the art). Antibodies directed against CD7 or K12 may serve as controls in certain assay formats. The antibodies of the present invention may be prepared by any of a variety of well-known methods.

One embodiment of the present invention that can be used to screen test compounds for their ability to affect the interaction of CD7 with K12 comprises the steps of forming a composition comprising a CD7 protein, a K12 protein, and the test compound; assaying for the level of interaction of the CD7 protein and the K12 protein; and comparing the level obtained in the presence of the test compound to that obtained in the absence of the test compound, such that if the level obtained differs, a compound that affects the interaction of the CD7 protein and the K12 protein is identified. Preferably, at least one of the CD7 protein and the K12 protein can be labeled with a detectable moiety. One of the CD7 protein or the K12 protein can be soluble, and the other can be bound, although alternative assay formats are possible and well known. The test compound can be added to the composition after addition of the CD7 protein and the K12 protein, before both proteins are added, or after one protein is added and before the other is added. The interaction of CD7 with K12 that may be influenced by the test compound includes reciprocal binding of CD7 and K12. For example, a test compound may partially or completely inhibit binding of CD7 and K12. This partial or complete inhibition of binding can be measured in various ways, such as determining the binding constant in the presence and absence of the test compound. In other embodiments, the binding affinity and/or binding avidity between CD7 and K12 may be measured with and without the test compound.

In another aspect, the screening methods of the invention comprise forming a composition comprising the test compound, the K12 protein and cells expressing CD7; determining the level of biological activity of the K12 protein in the composition; and comparing the level of biological activity with that which occurs in the absence of test compound, wherein a difference in the level of biological activity indicates that the test compound affects the biological activity of a K12 protein. Biological activity of K12 can be assayed in any number of ways, for example, by determining the phosphorylation state of intracellular proteins (activation of CD7 by agonist antibodies is known to induce phosphorylation of intracellular proteins), by determining the activation of NK cells and by determining the production of interferon gamma and/or GM-CSF. In a related aspect, the cells express K12 and soluble CD7, or cells expressing CD7, is used.

A particular example of an assay for the identification of potential CD7 or K12 antagonists is a competitive assay, which combines K12 and a candidate molecule with CD7 under the appropriate conditions for a competitive assay. Either CD7 or K12 can be labeled with a detectable moiety so that the binding can be measured and the effectiveness of the agonists or antagonist judged. The detectable moiety allows for detection by direct or indirect means. Direct means include, but are not limited to luminescence, chemiluminescence, fluorescence, radioactivity, optical or electron density. Indirect means include but are not limited to an enzyme or epitope tag.

A detectable moiety is a compound or molecule that is distinguishable from the surrounding meliu. The art is replete with examples of detectable moieties that are used in screening assays. In the present specification, the term "label" is used interchangeably with "detectable moiety." For example, detectable moieties may be any moiety based on luminescence, chemiluminescence, fluorescence, radioactivity, enzymatic reactions, colorimetric, optical or electron density. It is to be understood that the screening assays described herein for identifying test compounds that influence the K12/CD7 interaction may employ one or more of the detectable moieties known in the art. The CD7 and/or K12 proteins can be directly or indirectly labeled with a detectable moiety. Such moieties can be attached (i.e., "labeled") to the CD7 and/or K12 proteins by any suitable conventional procedure. The CD7 and/or K12 proteins comprise functional groups on amino acid side chains that can be reacted with functional groups on a desired moiety to form covalent bonds, for example. Alternatively, the CD7 and/or K12 proteins or detectable moiety can be derivatized to generate or attach a desired reactive functional group. The derivatization can involve attachment of one or more linkers or couplers, such as any of the family of bifunctional coupling reagents available for attaching various molecules to polypeptides (Pierce Chemical Company, Rockford, Ill.).

Molecules that inhibit or prevent the dissociation of the CD7/K12 complex can be identified by forming the complex in the absence of a candidate molecule, then adding the candidate molecule to the mixture, and changing the conditions so that, but for the presence of the candidate molecule, CD7 would be released from the complex. The concentration of the free or bound CD7 can then be measured and the dissociation constant of the complex could be determined and compared to a control.

Another method by which molecules can be identified that affect (either inhibit or promote) the interaction between CD7 and K12 is the solid phase method, in which CD7 is bound and placed in a medium with labeled K12. The amount of signal produced by the interaction between CD7 and K12 is measured in the presence and in the absence of a candidate molecule. Diminished levels of signal, in comparison to a control, indicate that the candidate molecule inhibited the interaction between CD7 and K12. Increased levels of signal, in comparison to a control, indicate that the candidate molecule promotes the interaction between CD7 and K12. In alternative embodiments, K12 could be bound and CD7 labeled. The CD7 and/or K12 proteins can be directly or indirectly labeled. For example, if the protein is recombinantly produced, one can engineer fusion proteins that can facilitate solubility, labeling, immobilization and/or detection. Fusion proteins which facilitate these processes can include, but are not limited to soluble Ig-tailed fusion proteins and His-tagged proteins. Methods for engineering such soluble Ig-tailed fusion proteins are well known to those of skill in the art. See, for example, U.S. Pat. No. 5,116,964, and the illustrative embodiments described below. Indirect labeling involves the use of a protein, such as a labeled antibody, which specifically binds to a component of the assay.

In other embodiments, additional homogeneous assay formats are used, such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence. In another aspect, the inventive methods utilize heterogeneous assay formats such as enzyme-linked immunosorbant assays (ELISA) or radioimmunoassays. In yet another aspect of the invention are cell-based assays, for example those utilizing reporter genes, as well as functional assays that analyze the effect of an antagonist or agonist on biological function(s) (i.e., K12/CD7 "biological activity").

One such assay is based on fluorescence resonance energy transfer (FRET; for example, HTRF®, Packard BioScience Company, Meriden, Conn.; LANCE™, PerkinElmer LifeSciences, Wallac Oy., Turku, Finland) between two fluorescent labels, an energy donating long-lived chelate label and a short-lived organic acceptor. The energy transfer occurs when the two labels are brought in close proximity via the molecular interaction between CD7 and K12. In a FRET assay for detecting inhibition of the binding of CD7 and K12, europium chelate or cryptate labeled CD7 or K12 serves as an energy donor and streptavidin-labeled allophycocyanin (APC) bound to the appropriate binding partner (i.e., K12 if CD7 is labeled, or CD7 if K12 is labeled) serves as an energy acceptor. Once CD7 associates with K12, the donor and acceptor molecules are brought in close proximity, and energy transfer occurs, generating a fluorescent signal at 665 nm. Antagonists of the interaction of CD7 and K12 will thus inhibit the fluorescent signal, whereas agonists of this interaction would enhance it.

Another useful assay is a bioluminescence resonance energy transfer, or BRET, assay, substantially as described in Xu et al., Proc. Natl. Acad. Sci. USA 96:151 (1999). Similar to a FRET assay, BRET is based on energy transfer from a bioluminescent donor to a fluorescent acceptor protein. However, a green fluorescent protein (GFP) is used as the acceptor molecule, eliminating the need for an excitation light source. Exemplary BRET assays include BRET and BRET$^2$ from Packard BioScience, Meriden, Conn. It is understood that CD7 and K12 may be configured in the assay in any workable manner, such as alternatively labeling CD7 or K12 with GFP. It is further understood that agonists and antagonists of the CD7 and K12 interaction may be identified as described above for the FRET assay.

DELFIA® (dissociated enhanced lanthanide fluoroimmunoassay; PerkinElmer LifeSciences, Wallac Oy., Turku, Finland) is a solid-phase assay based on time-resolved fluorometry analysis of lanthanide chelates (see, for example, U.S. Pat. No. 4,565,790 issued Jan. 21, 1986). For this type of assay, microwell plates are coated with a first protein (CD7 or K12). The binding partner (CD7 or K12, as the case may be) is conjugated to europium chelate or cryptate, and added to the plates. After suitable incubation, the plates are washed and a solution that dissociates europium ions from solid phase bound protein, into solution, to form highly fluorescent chelates with ligands present in the solution, after which the plates are read using a reader such as a VICTOR$^{2}$™ (PerkinElmer LifeSciences, Wallac Oy., Turku, Finland) plate reader to detect emission at 615 nm).

Another assay that may be employed is a FlashPlate® (Packard Instrument Company, Ill.)-based assay. This assay measures the ability of compounds to inhibit protein—protein interactions. FlashPlates® are coated with a first protein (either CD7 or K12), then washed to remove excess protein. For the assay, compounds to be tested are incubated with the second protein (K12, if the plates are coated with CD7, or CD7 if plates are coated K12) and $I^{125}$ labeled antibody against the second protein and added to the plates. After suitable incubation and washing, the amount of radioactivity bound is measured using a scintillation counter (such as a MicroBeta® counter; PerkinElmer LifeSciences, Wallac Oy., Turku, Finland).

Further embodiments include the AlphaScreen™ assay (Packard Instrument Company, Meriden, Conn.). AlphaScreen™ technology is an "Amplified Luminescent Proximity Homogeneous Assay" method utilizing latex microbeads (250 nm diameter) containing a photosensitizer (donor beads), or chemiluminescent groups and fluorescent acceptor molecules (acceptor beads). Upon illumination with laser light at 680 nm, the photosensitizer in the donor bead converts ambient oxygen to singlet-state oxygen. The excited singlet-state oxygen molecules diffuse approximately 250 nm (one bead diameter) before rapidly decaying. If the acceptor bead is in close proximity to the donor bead (i.e., by virtue of the interaction of CD7 and K12), the singlet-state oxygen molecules reacts with chemiluminescent groups in the acceptor beads, which immediately transfer energy to fluorescent acceptors in the same bead. These fluorescent acceptors shift the emission wavelength to 520–620 nm, resulting in a detectable signal. Antagonists of the interaction of CD7 and K12 will thus inhibit the shift in emission wavelength, whereas agonists of this interaction would enhance it.

Without being bound or limited to the specifics of the following, one example of a cell-based binding assay procedure is as follows. A recombinant expression vector containing the CD7 cDNA is constructed. CV1-EBNA-1 cells in 10 cm$^2$ dishes are transfected with this recombinant expression vector. CV-1/EBNA-1 cells (ATCC CRL 10478) constitutively express EBV nuclear antigen-i driven from the CMV Immediate-early enhancer/promoter. CV1-EBNA-1 was derived from the African Green Monkey kidney cell line CV-1 (ATCC CCL 70), as described by McMahan et al., (EMBO J. 10:2821, 1991). The transfected cells are cultured for 24 hours, and the cells in each dish then are split into a 24-well plate. After culturing an additional 48 hours, the transfected cells (about $4 \times 10^4$ cells/well) are washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated for 1 hour at 37° C. with various concentrations of, for example, a soluble K12 polypeptide/Fc fusion protein. In addition, a test compound may be added prior to, concurrent with or subsequent to combining the soluble K12 polypeptide/Fc fusion protein and CD7-expressing cells. Cells then are washed and incubated with a constant saturating concentration of a $^{125}$I-mouse anti-human IgG in binding medium, with gentle agitation for 1 hour at 37° C. After extensive washing, cells are released via trypsinization. The mouse anti-human IgG employed above is directed against the Fc region of human IgG and can be obtained from Jackson Immunoresearch Laboratories, Inc., West Grove, Pa. The antibody is radiiodinated using the standard chloramine-T method. The antibody will bind to the Fc portion of any polypeptide/Fc polypeptide that has bound to the cells. In all assays, non-specific binding of $^{125}$I-antibody is assayed in the absence of the Fc fusion polypeptide/Fc, as well as in the presence of the Fc fusion polypeptide and a 200-fold molar excess of unlabeled mouse anti-human IgG antibody. Cell-bound $^{125}$I-antibody is quantified on a Packard Autogamma counter. Affinity calculations (Scatchard, Ann. N.Y. Acad. Sci. 51:660, 1949) are generated on RS/1 (BBN Software, Boston, Mass.) run on a Microvax computer. A working example of such an assay is provided in Example 5. Of course it is understood that one of skill in the art may reformat the assay to have K12 expressed on the surface of the cells and use a soluble version of CD7 as the labeled probe. In addition, various detectable moieties, as described above, may be used instead of the Cell proliferation, cell activation, cell death, cell differentiation, cytokine production and cell adhesion assays may also be used to screen for test compounds that enhance or inhibit CD7/K12-associated biological effects. Exemplary biological readout assays that are designed to determine the affect a test compound has on CD7/K12-associated biological activity include, but are not limited to: phosphorylation of intracellular proteins; adhesion of hematopoietic cells to fibronectin, ICAM-1, and V-CAM1; regulation of beta 1 integrins on NK cells; cell proliferation in allogeneic and autologous mixed lymphocyte reactions (including activation and/or proliferation of T and NK cells); myeloid cell-based cytotoxicity (including T and NK cells); induction of cytokines and other soluble factors, such as interferon gamma and GM-CSF; and, HIV-1 infectivity and syncytia formation. Of course it is understood that the cell-based screening assays described above would measure the affect a test compound has on CD7:K12 binding and the subsequent biological activity resulting therefrom as defined by the biological readout. Exemplary embodiments of such biological readout assays that can be used to screen test compounds may be found in Examples 8, 9 and 10.

Assays for cytokine production and/or proliferation of spleen cells, lymph node cells or thymocytes include, without limitation, those described in: Kruisbeek and Shevach, 1994, Polyclonal T cell stimulation, in Current Protocols in Immunology, Coligan et al. eds. Vol 1 pp. 3.12.1–3.12.14, John Wiley and Sons, Toronto; and Schreiber, 1994, Measurement of mouse and human interferon gamma in Current Protocols in Immunology, Coligan et al. eds. Vol 1 pp. 6.8.1–6.8.8, John Wiley and Sons, Toronto. These assays are well known in the art and need not be reviewed in detail. Such assays may be readily adapted by one of ordinary skill in the art to provide a screening assay to determine what effect a test compound has on CD7:K12-associated cytokine production and/or proliferation in various cells.

Assays for cell movement and adhesion include, without limitation, those described in: Current Protocols in Immunology Coligan et al. eds, Greene Publishing Associates and Wiley-Interscience (Chapter 6.12, Measurement of alpha and beta chemokines 6.12.1–6.12.28); Taub et al. J. Clin. Invest. 95:1370–1376, 1995; Lind et al. APMIS 103:140–146, 1995; Muller et al Eur. J. Immunol. 25: 1744–1748; Gruber et al. J Immunol. 152:5860–5867, 1994; Johnston et al. *J Immunol.* 153: 1762–1768, 1994.

Assays for receptor-ligand activity include without limitation those described in: Current Protocols in Immunology Coligan et al. eds, Greene Publishing Associates and Wiley-Interscience (Chapter 7.28, Measurement of cellular adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

Thus, the present invention encompasses methods of screening candidate molecules for their ability to modulate the interaction of CD7 and K12, and their ability to modulate activities mediated by the interaction of CD7 and K12. By observing the effect that the candidate molecule has on the known binding characteristics of CD7, K12 or fragments thereof, compounds that inhibit or enhance the interaction of CD7 and K12 can be identified. Typical test compounds are small molecules, antibodies, or peptides and can be part of extensive small molecule libraries developed for use in screening methods. The term "small peptides" includes peptidomimetics. In this context, the identification of small molecules which interact with the CD7 protein and/or the K12 ligand can be used to develop drugs that modulate the activation pathway and can allow physicians to treat distinct immune conditions without the negative side effects present in current therapies.

Indications and Formulations

Thus, in one aspect, the invention provides methods of treating diseases mediated by CD7 and/or K12, the method comprising administering to a mammal in need thereof an effective amount of a K12 protein and small molecules identified as being agonists of the interaction of CD7 and K12. The K12 protein can be a soluble form of the protein, and preferably can be a multimeric fusion protein such as, for example, a Fc fusion. Diseases that are mediated by the interaction between CD7 and K12 and that can be treated using K12 protein include HIV-1 infection, cancers (especially T cell lineage neoplasias, e.g., T cell leukemia, acute lymphomic leukemia, cutaneous T cell lymphoma), and infections including bacterial and viral infections (e.g., CMV and EBV infections).

In an alternative aspect, the invention provides a method of treating a disease mediated by CD7 and/or K12, the method comprising administering to a mammal in need thereof an effective amount of a K12 antagonist. An example of a K12 antagonist is a neutralizing antibody to K12. The generation of antibodies to extracellular portions of K12 molecules are well known to those skilled in the art. Antibodies can be polyclonal or monoclonal, and full length or fragments (e.g., Fab and Fab2 fragments). Preferably, for use in humans, the antibodies are human or humanized; techniques for creating such human or humanized antibodies are also well known and are commercially available from, for example, Medarex Inc. (Princeton, N.J.) and Abgennix Inc. (Fremont, Calif.). Antibodies can be screened for their ability to neutralize the biological effects of K12 using the screening assays described herein. Examples of diseases that can be mediated by CD7 and that can be treated with antagonists of K12 include sepsis, graft vs. host disease due to transplantation, autoimmune diseases including multiple sclerosis, arthritis such as, for example, rhumatoid arthritis and psoriatic arthritis, scleroderma, lupus, psoriasis, atopic dermatitis, type I diabetes mellitus, Hashimoto's thyroiditis, pernicious anemia, Addison's disease, myasthenia gravis, uveitis, psoriasis, Guillain-Barre Syndrome, Grave's disease, systemic lupus erythematosus and dermatomyositis, asthma, eczema, atopical dermatitis, contact dermatitis, other eczematous dermatitides, seborrheic dermatitis, and allergic rhinitis.

The terms "treat", "treating", and "treatment" used herein includes curative, preventative (e.g., prophylactic) and palliative treatment.

For such therapeutic uses, the identified agonists or antagonists of the interaction between CD7 and K12, CD7, and/or K12 can be administered to the mammal in need through well-known means, including oral, parenterally (e.g., subcutaneous, intramuscular, intravenous, intradermal, etc. injection), buccal, rectal, topically, or via inhalation and/or insufflation. Compounds are usually formulated with a suitable carrier. Formulations suitable for administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents.

The identified compounds that affect the interaction between CD7 and K12 can be administered to a patient at therapeutically effective doses to treat or ameliorate diseases associated with the activity of CD7 and/or K12. A therapeutically effective dose refers to that amount of the compound sufficient to result in amelioration of symptoms of the disease. The dosage will depend on the specific activity of the agonist or antagonist and can be readily determined by routine experimentation. For example, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture, while minimizing toxicities. Such information can be used to more accurately determine useful doses in humans. The amount and timing of compound administered will be dependent upon the subject being treated, on the severity of the affliction, on the manner of administration and upon the judgment of the prescribing physician.

The following examples are offered by way of illustration, and not by way of limitation. Those skilled in the art will recognize that variations of the invention embodied in the examples can be made, especially in light of the teachings of the various references cited herein, the disclosures of which are incorporated by reference in their entirety.

EXAMPLE 1

Cloning of the Human and Mouse K12 and CD7 Genes

The human K12 protein was cloned based on the published sequence (Slentz-Kesler, 1998) using RT-PCR from MRNA prepared from the K562 erythroleukemia cell line. A mouse protein related to the human K12 sequence was identified as an EST (AA734402) from a proximal colon cDNA library. The EST was purchased and sequenced in its entirety. After the correct sequence was determined, it was found that the cDNA encoded a 212 amino acid transmembrane protein that shares 36% overall amino acid identity over its entire length with the human K12 protein. Homology over the extracellular portion was slightly higher.

The mouse CD7 gene was cloned using PCR from an EL4.6 λ zap library. All cDNA clones were sequenced on both strands to confirm that no amino acid changes had been introduced by PCR into the published CD7 sequence (Yoshikawa, *Immunogenetics* 27:114 (1993); Yoshikawa, *Immunogenetics* 41:159 (1995)).

EXAMPLE 2

Generation of K12-Fc Fusion Proteins

Both the human and mouse K12-Fc fusion proteins were made by using Sew-PCR to attach the Fc portion of human IgG1 (see U.S. Pat. No. 5,457,035 for a description of the Fc portion) to that part of the gene encoding the extracellular domain of human K12 (amino acids 1–145 in the human clone (SEQ ID NO:4) (Slentz-Kesler, 1998), and amino acids 1–160 in the murine clone (SEQ ID NO:8)). The fusion proteins were transiently expressed in CV-1/EBNA cells and purified from the conditioned medium using protein A Sepaharose (Pharmacia, Piscataway, N.J.) and standard techniques. Because of the fusion to Fc sequences, these fusion proteins exist as dimers in solution.

EXAMPLE 3

Precipitation of a K12-Fc Binding Protein from NK Cells

Primary human NK cells ($1 \times 10^6$ cells/ml) were radiolabeled overnight with 50 uCi/ml [$^{35}$S]-cysteine/methionine) (ProMix, Amersham, Arlington, Ill.). Radiolabeled cells were lysed with 1 ml RIPA E lysis buffer (PBS, 1% Triton). 150 ul of lysate were incubated with 1 ug of HuK12-Fc or a control Fc fusion protein for 1 hour at 4°. Precipitated proteins were collected onto Protein A Sepharose and loaded separated onto a 4–20% acrylamide gradient Tris-Glycine gel (Novex, San Diego, Calif.) under denaturing, reducing conditions. The gel was fixed, treated with Amplify (Amersham, Arlington, Ill.), dried, and exposed to XAR-5 film. A single protein band of approximately 40 kDa was precipitated from the NK cells, indicating that expression cloning might be a viable way to identify the K12 cognate.

EXAMPLE 4

Cloning of the K12 Cognate from a Human PBT cDNA Expression Library

The human peripheral blood T cell library cDNA expression library was constructed in the pDC409 vector using methods previously described (McMahan, *EMBO J.* Vol. 10:2821 (1991)) and contained about $0.5 \times 10$ cDNA clones. Approximately 78% of clones in the library contain inserts, and the average insert size is about 1.2 Kb. The K12-Fc fusion protein was used to screen the expression library and fifty pools of approximately 1600 cDNAs each were transfected into CV-1/EBNA cells. Two days later the transfected cells were tested for their capacity to bind the K12-Fc fusion protein. Two positive pools were identified. These cDNA pools were subsequently subdivided into smaller and smaller groups and assayed until single positive cDNA clones were isolated from each original pool. Sequencing of these cDNAs and comparison with public DNA databases revealed that the cDNA from each positive pool encoded a full length clone of the human CD7 gene. This result explained why the size of the protein precipitated from NK cell lysates in Example 3 (40 kDa) was identical to the reported size of human CD7 (Haynes, *Immunol. Rev.* 57:127 (1981); Aruffo, *Embo J.* 6:3313 (1987)).

EXAMPLE 5

K12/CD7 Binding Studies

COS-1 cells were transfected with an expression vector encoding full length HuCD7 (human CD7), HuCD7-TR (human CD7 containing an internal deletion of the 36 amino acid tandem repeat), MuCD7 and vector only cDNA using DEAE-Dextran. However, any of a large number of expression vectors that are commercially available from numerous companies (e.g., Clontech Inc., Palo Alto, Calif.) could also be used to express the desired cDNAs. Two days post transfection the cells were assayed for the capacity to bind HuK12-Fc as previously described for other Fc fusion proteins (Lyman et al.,1993, *Cell* 75:1157–1167) with the following modifications. The binding media (RPMI 1640, 1%FBS, 0.02% NaAzide, 20 mM HEPES, pH7.2) was modified to include imM $MnCl_2$. In some experiments, the transfected cells were incubated with zero, 20 ug/ml or 2 mg/ml of Con A in BM/MM prior to binding with the Fc proteins. Following incubation for 30 minutes at room temperature and the continued presence of Con A, 1 ug/ml of either HuK12-Fc or MuK12-Fc was then added to the appropriate slides. Binding of the Fc protein was detected with [$^{125}$I] mouse anti-Human Fc antibody as previously described (Lyman, 1993). After binding the iodinated antibody, the cells were washed and then the radioactivity was quantitated by Storm Phosphorimager.

The results demonstrated that cells transfected with the full length HuCD7 construct bound HuK12-Fc best; when the cells were transfected with the truncated HuCD7-TR construct, relative binding of the labeled HuK12-Fc was about 10 fold less than to cells expressing the full length HuCD7 construct. However, binding of HuK12-Fc to the cells expressing murine CD7 was approximately 4 fold less than binding to cells expressing the full length HuCD7. Binding to the cells transfected with vector alone was, as expected, negligible.

The complementary experiments were also performed to assay the binding of either human or murine CD7-Fc fusion proteins to cells transfected with either human or murine K12 expression plasmids (full length). The binding assays were done as described above. Human CD7-Fc bound to the surface of cells transfected with a full length human K12 cDNA expression vector, and murine CD7-Fc bound to cells transfected with a full length murine K12 cDNA expression vector. However, only background binding (indistinguishable from negative controls) was observed when human CD7-Fc fusion protein was assayed against cells transfected with a full length murine K12 cDNA, or when murine CD7-Fc fusion protein was assayed against cells transfected with a full length human K12 cDNA.

These results demonstrate that a binding assay based on the interaction of CD7 and K12 that provides a means of assaying for the level of interaction between the CD7 protein and the K12 protein is possible. It further establishes the foundation for other assay formats to screen for test compounds that influence the interaction of CD7 and K12.

EXAMPLE 6

Monoclonal Antibodies to Human CD7 Block Binding of K12-Fc

Six commercial antibodies to the extracellular domain of human CD7 were tested for their capacity to block the binding of K12-Fc to Jurkat cells, which express high levels of CD7. Monoclonal antibodies directed against human CD7 that were tested were the following: Clone M-T701 (Becton Dickinson, Franklin Lakes, N.J.); Clone 8118.1 (Immunotech, Westbrook, Me.); Clone 4H9 (Pharmingen, San Diego, Calif.); and Clones RFI-2a, WM31, and CLB-3A1 (Research Diagnostics, Inc., Flanders, N.J.). The calculated results are shown in the tables below.

TABLE 1 shows the reductions in the percentage of positive cells and mean fluorescence intensity that occur when Jurkat cells are preincubated with human K12-Fc fusion protein prior to staining the cells with the antibodies.

TABLE 1

| Primary | Non-Blocked | | Preblocked w/HuK12-FC | |
|---|---|---|---|---|
| Antibody | % Positive Cells | MFI | % Positive Cells | MFI |
| M-T701 | 78% | 27 | 12% | 19 |
| 8118.1 | 78% | 27 | 8% | 24 |
| 4H9 | 88% | 38 | 4% | 19 |
| RFT-2a | 71% | 23 | 9% | 18 |
| WM31 | 62% | 22 | 11% | 18 |
| CLB-3A1 | 80% | 30 | 63% | 24 |
| IgG Control | 3% | 18 | | |

TABLE 2 shows that, in a similar fashion, preincubation of the Jurkat cells with the six anti-human CD7 antibodies blocks the binding (to varying degrees) of human K12-Fc to the cells.

TABLE 2

| Primary | Non-Blocked | | Preblocked w/indicated Mab | |
|---|---|---|---|---|
| Protein | % Positive Cells | MFI | % Positive Cells | MFI |
| HuK12Fc | 98% | 95 | 85% 4H9 | 30 |
| | | | 62% 8118.1 | 23 |
| | | | 6% M-T701 | 16 |
| | | | 80% RFT-2a | 27 |
| | | | 12% WM31 | 17 |
| | | | 73% CLB-3A1 | 27 |
| | | | 97% IgG Control | 94 |
| Control Fc | 3.4% | 18 | | |
| IgG control | 3.6% | 17 | | |

Thus, the K12-Fc fusion protein blocked the binding of each of the antibodies to Jurkat cells to varying degrees, and each member of the panel of monoclonal antibodies could interfere with the ability of K12-Fc to bind to CD7 on Jurkat cells.

These results demonstrate that screening assays of the present invention are capable of identifying test compounds that influence the level of interaction of CD7 and K12. More specifically, these results demonstrate that antagonists may be identified by assaying for the level of interaction of CD7 and K12 in the presence and absence of the test compound. It further establishes the foundation for other assay formats to screen for test compounds that influence the interaction of CD7 and K12.

EXAMPLE 7

Chromosomal Location of the Mouse K12 Gene

The chromosomal location of the mouse K12 protein was determined using the Jackson Laboratory radiation hybrid panel mapping resource (Flaherty, *Mamm. Genome* 9:417–418 (1998)). The murine K12 protein maps on mouse chromosome 11, proximal to CD7 locus.

EXAMPLE 8

K12-Fc Blocks Con A, but not Anti-TcR-induced Cell Proliferation

The mouse K12-Fc fusion protein was tested for its capacity to inhibit the proliferation of lymph node cells (from BALB/c mice) that had been stimulated with either soluble Con A or immobilized anti-TcR $\alpha/\beta$. The K12-Fc fusion protein inhibited Con A induced proliferation of the cells in a dose-dependent manner, but had no effect on anti-TcR induced cell proliferation. Since Con A is known to bind to a number of proteins, including CD7, the inhibition of Con A-induced T cell proliferation by K12-Fc could simply be due to K12 blocking Con A binding to CD7. Whether Con A could inhibit K12-Fc binding to COS-1 cells transfected with cDNAs encoding CD7 was then examined. No blocking of either human K12-Fc (added at a concentration of 1 ug/ml) to human CD7 or mouse K12-Fc (added at a concentration of 1 ug/ml) to mouse CD7 was seen when the cells were preincubated with 20 ug/ml of Con A. When the amount of Con A in the medium was raised to 2 mg/ml, a 30% inhibition of human K12-Fc binding and about 90% inhibition of mouse K12-Fc binding was observed. Given that the concentration of ConA used in the cell proliferation experiment was 1 $\mu$g/ml, it seems unlikely that the inhibitory effect of K12-Fc on the proliferation of lymph node cells was due to the blocking of ConA binding to the cells. Thus, K12-Fc inhibits ConA-induced proliferation of lymph node cells.

These experiments establish that cell-based assays having a biological readout may be adapted to screen for test compounds. In addition, these studies demonstrate that the biological effects of the K12/CD7 interaction may be measured or assayed in a screening assay format. Furthermore, these studies establish the foundation for other cell-based assay formats using a biological readout, such as those described above, to screen for test compounds that influence the interaction of CD7 and K12 and consequently the biological effects of the K12/CD7 interaction.

EXAMPLE 9

Human K12-Fc Mediated Human NK Cell Activation

The capacity of K12 to induce human NK cell activation through its interaction with CD7 was analyzed by examining the expression of surface molecules associated with cellular activation.

Human NK cells were prepared from normal donor peripheral blood. PBMC were isolated by standard techniques from 200 ml of donor 362 heparinized whole blood. Prior to NK enrichment macrocytes and monocytes were depleted from PBMC by plastic adherence. NK cells were then enriched by negative selection. $CD3^+$, $CD19^+$ and MHC class $II^+$ cells were removed using biotinylated mAb specific for these markers followed by incubation with streptavidin-coated magnetic beads. This procedure was completed twice resulting in an enriched population of human $CD56^+$ NK cells.

For in vitro NK cell activation assays, enriched NK cells were added to tissue culture wells that had been treated with mu/hu IgG, huCD7 mAb or huK12-Fc that had been immobilized onto the plastic well at a concentration of 2.5 ug/ml. These cultures were incubated for 20 hours at 37° C. and then expression of CD25 and CD69, and the adhesion molecule CD54, evaluated by flow cytometry. Increased expression of the early activation marker CD69 and of the IL-2 receptor alpha chain (CD25) indicates that the NK cells have received an activation signal. The results of two experiments using the NK preparation from donor 362, which was about 92% $CD56^+$, are shown in TABLE 3 below. These results demonstrate that immobilized huK12-Fc and immobilized huCD7 mAb induce activation of human NK cells.

TABLE 3

| Immobilized Protein | Relative Expression of Marker on Cell Surface | | | |
|---|---|---|---|---|
| | Control mAb | CD25 | CD69 | CD54 |
| mu/hu IgG | 2 | 7 | 15^ | 12 |
| (2.5 µg/ml) | 5 | 9 | 24^^ | |
| HuCD7 mAb | 5 | 16 | 18^ | 43 |
| (2.5 µg/ml) | 6 | 12 | 60^^ | |
| HuK12-Fc | 7 | 38 | 57^ | 62 |
| (2.5 µg/ml) | 16 | 9 | 48^^ | |

^results expressed as Mean Fluorescence Intensity (MFI).
^^results expressed as % positive cells.

Thus, in two separate experiments, immobilized huK12-Fc, and to a lesser extent immobilized huCD7 mAb, induced activation of a preparation of human NK cells from donor 362. Addition of anti-CD7 antibodies or K12-Fc in solution (not immobilized) to NK cultures did not result in enhancement of cell surface molecule expression.

In other experiments, two different NK cell donors did not demonstrate significant activation induction by huK12-Fc, indicating either that activation of fresh NK cells through CD7 demonstrates donor variability or that the kinetics of activation of different donors may be different. This lack of effect in different donors may be due to examining at a 20 hour time point when optimal activation induced by huK12 may be 24 hours or even later.

As with the previous example, these studies further establish that cell-based assays having a biological readout may be adapted to screen for test compounds. These studies also demonstrate that the biological effects of the K12/CD7 interaction may be measured or assayed in a screening assay format.

EXAMPLE 10

Human K12 Inhibits Syncytia Formation

In this experiment, a fusion inhibition assay was performed to test the antiviral activity of soluble forms of CD7 and K12.

H9 cells infected with HIV-1 MN virus and SupT1 cells were harvested at log phase ($5\times10^4$/ml) by centrifuging cells for 8 minutes at 1,500 rpm. The cells were resuspended in 20 ml of R10 and centrifuged again at 1500 rpm. The cells were counted to determine cell number and viability.

The cells were resuspended at concentrations of 30,000 cells/25 μl (SupT1) or 10,000/25 μl (H9/MN). A mixture of 10,000 cells of H9/MN and 30,000 SupT1 were distributed on 96 well tissue culture plates. Soluble K12 poly-His Flag (hu K12 HF), soluble K12/hu IgG1 Fc fusion protein (hu K12:Fc), and soluble CD7 poly-His Flag at varied concentrations were added to duplicate wells.

Twenty four hours later, each of the wells was examined under an inverted microscope. The syncytia were counted in each well by dividing the well into three equal fields. Two controls were also examined: human CD4 as a positive control (AIDS Research and Reference Reagent Program Catalog No. 1813) and wild type Rev protein as a negative control (AIDS Reference and Reagent Program Catalog No. 1457). Any cell with the appearance of multiple syncytia which was at least three times the size of a single control cell, or any cell or group of cells which was associated with a balloon/bubble-like structure, was considered a syncytium.

The different treatment groups at each concentration were compared to each other and to control groups in terms of statistical significance. FIG. 2 is a composite graph illustrating the effect of soluble K12 poly-His Flag (hu K12 HF), soluble K12/hu IgG1 Fc fusion protein (hu K12:Fc), and soluble CD7 poly His flag at varied concentrations on syncytia numbers. All three compounds have inhibitory activity against HIV-1 when measured by the ability to inhibit multinucleated syncytia formation between HIV-1 infected H9 and SupT1 cells. Specifically, the three compounds were equally effective as the positive control CD4 in inhibiting syncytia formation at concentrations of 16, 4, 1, and 0.25 μg/ml. At 64 μg/ml, CD4 appears to be more effective than CD7 or K12 compounds at inhibiting syncytia formation. CD7 and K12 compounds were more effective than the negative control at inhibiting syncytia formation. These results demonstrate that, like CD4, soluble forms of CD7 and/or K12 can be used to treat HIV-1, and should be effective in inhibiting the transmission of HIV-1 between cells and between individuals, and at reducing the viral load in infected individuals.

What is claimed is:

1. A method of screening a test compound to identify its ability to affect the binding between CD7 and K12, the method comprising the steps of:

a. forming a composition comprising a CD7 protein that binds
   i) a K12 protein from the same species as the CD7 protein, or
   ii) a protein having at least 90% sequence identity to said K12 protein, wherein the proein binds said CD7 protein; the K12 protein of i) or ii): and,
   a test compound;
b. assaying for the level of binding between the CD7 protein and the K12 protein; and
c. comparing the level obtained in (b) to that obtained in the absence of the test compound, such that if the level obtained in (b) differs from that obtained in the absence of test compounds a compound that affects the binding of the CD7 protein and the K12 protein is identified.

2. The method of claim 1, wherein at least one of the CD7 protein and the K12 protein is labeled with a detectable moiety.

3. The method of claim 1, wherein the test compound is a small organic molecule.

4. The method of S9 wherein at least one of the CD7 protein or the K12 protein is soluble.

5. The method of claim 1, wherein the test compound is added to the composition after addition of the K12 protein.

6. The method of claim 1, wherein the test compound is an antibody.

7. The method of claim 1, wherein the test compound is a peptide.

8. A method of screening a test compound to identify its ability to affect the binding between CD7 and K12, the method comprising the steps of:

a. forming a composition comprising a K12 protein that binds
   i) a CD7 protein from the same species as the K12 protein, or
   ii) a protein having at least 90% sequence identity to said CD7 proteins wherein the protein binds said K12 protein;
   the CD7 protein of i) or ii); and,
   a test compound;
b. assaying for the level of binding between the CD7 protein and the K12 protein; and
c. comparing the level obtained in (b) to that obtained in the absence of the test compound, such that if the level obtained in (b) differs from that obtained in the absence of test compounds a compound that affects the binding of the CD7 protein and the K12 protein is identified.

9. The method of claim 8, wherein at least one of the CD7 protein and the K12 protein is labeled with a detectable moiety.

10. The method of claim 8, wherein the test compound is a small organic molecule.

11. The method of claim 8, wherein the test compound is an antibody.

12. The method of claim 8, wherein the test compound is a peptide.

13. The method of claim 8, wherein at least one of the CD7 protein or the K12 protein is soluble.

14. The method of claim 8, wherein the test compound is added to the composition after addition of the K12 protein.

* * * * *